United States Patent
Ben-Noon

(10) Patent No.: US 10,980,780 B2
(45) Date of Patent: *Apr. 20, 2021

(54) METHODS AND COMPOSITIONS OF ANTI-INFLAMMATORY DRUG AND DICER ACTIVATOR FOR TREATMENT OF NEURONAL DISEASES

(71) Applicant: NeuroSense Therapeutics Ltd., Herzellya (IL)

(72) Inventor: Alon Ben-Noon, Ramat-Hasharon (IL)

(73) Assignee: NEUROSENSE THERAPEUTICS LTD., Herzeliya (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/855,720

(22) Filed: Apr. 22, 2020

(65) Prior Publication Data

US 2020/0316026 A1 Oct. 8, 2020

Related U.S. Application Data

(63) Continuation of application No. 16/623,467, filed as application No. PCT/IL2018/050684 on Jun. 20, 2018.

(60) Provisional application No. 62/522,157, filed on Jun. 20, 2017.

(51) Int. Cl.
*A61K 31/415* (2006.01)
*A61K 31/496* (2006.01)
*A61P 25/00* (2006.01)

(52) U.S. Cl.
CPC .......... *A61K 31/415* (2013.01); *A61K 31/496* (2013.01); *A61P 25/00* (2018.01)

(58) Field of Classification Search
CPC ...... A61K 31/415; A61K 31/496; A61P 25/00
See application file for complete search history.

(56) References Cited

U.S. PATENT DOCUMENTS

| | | |
|---|---|---|
| 2006/0183698 A1 | 8/2006 | Abelson |
| 2015/0050345 A1 | 2/2015 | Smyth et al. |
| 2015/0086616 A1 | 3/2015 | Lehrer |

FOREIGN PATENT DOCUMENTS

| | | | |
|---|---|---|---|
| IL | WO 2014/020608 | * | 2/2014 |
| WO | 2013/139861 A1 | | 9/2013 |
| WO | 2014/020608 A1 | | 2/2014 |

OTHER PUBLICATIONS

Drachman et al. in Annals of Neurology 52:771-778 (2002) (Year: 2002).*
FDA Guidance for Industry 2005 at https://www.fda.gov/media/72309/download. (retrieved from the internet Sep. 11, 2020) (Year: 2005).*
Owens et al. in Clinical Infectious Diseases 41:S144-57 (2005) (Year: 2005).*
Goodman and Gilman's The Pharmacological Basis of Therapeutics (Tenth Edition (2001), McGraw Hill, Chapter I, pp. 3-29 (Year: 2001).*
International Search Report and Written Opinion dated Oct. 10, 2018 issued by the European Patent Office in international application No. PCT/IL2018/050684 filed Jun. 20, 2018.
Yoshino, T. et al., "Celecoxib does not induce convulsions nor does it affect GABA" A receptor binding activity in the presence of new quinolones in mice, European Journal of Pharmaco, Elsevier Science, NL, vol. 507, No. 1-3, Jan. 10, 2005, pp. 69-76.
Klegeris, A. et al., "Non-steroidal anti-inflammatory drugs (NSAIDs) and other anti-inflammatory agents in the treatment of neurodegenerative disease", Current Alzheimer Rese, Bentham Science Publ. Ltd., NL, vol. 2, No. 3, Jan. 1, 2005, pp. 355-365.
Cudkowicz, M.E. et al., "Trial of celecoxib in amyotrophic lateral sclerosis", Annals of Neurology., vol. 60, No. 1, Jan. 1, 2006, pp. 22-31.
Asadabadi, M. et al., "Celecoxib as adjunctive treatment to risperidone in children with autistic disorder: a randomized, double-blind, placebo-controlled trial", Psychopharamacology, Springer, Berlin, DE, vol. 225, No. 1, Jul. 11, 2012, pp. 51-59.
Amrite, A. et al., "Delivery of celecoxib for treating diseases of the eye: influence of pigment and diabetes", Expert Opinion on Drug Delivery, vol. 7, No. 5, Mar. 7, 2010, pp. 631-645.

* cited by examiner

*Primary Examiner* — Dennis Heyer

(74) *Attorney, Agent, or Firm* — JMB Davis Ben-David

(57) ABSTRACT

The present invention discloses compositions, means and kits thereof for treating neuronal clinical indications in a mammalian subject. The composition comprises, inter alia, a synergistic combination of an anti-inflammatory drug and a DICER activator. The present invention further discloses methods for treating neuronal diseases including Motor neuron diseases (MNDs), ALS, FTD (Frontotemporal Dementia), macular degeneration (AMD) autism, and neurodegenerative diseases such as Parkinson's disease and Alzheimer's disease.

19 Claims, 17 Drawing Sheets

METHODS AND COMPOSITIONS OF ANTI-INFLAMMATORY DRUG AND DICER ACTIVATOR FOR TREATMENT OF NEURONAL DISEASES

RELATED APPLICATIONS

This application is a continuation of U.S. application Ser. No. 16/623,467, filed Dec. 17, 2019, which is a U.S. national phase application under 35 U.S.C 371 of PCT International Application No. PCT/IL2018/050684, filed Jun. 20, 2018, which claims the benefit of and priority to U.S. Provisional application No. 62/522,157, filed Jun. 20, 2017, the entire disclosures of each of which are incorporated herein by reference in their entireties.

FIELD OF THE INVENTION

The present invention pertains to compositions, means, and kits for treating neuronal clinical indications in a mammalian subject. The composition comprises, inter alia, a synergistic combination of an anti-inflammatory drug and a DICER activator. Specifically, the present invention pertains to neuronal diseases including Motor neuron diseases (MNDs), ALS, FTD (Frontotemporal Dementia), macular degeneration (AMD), autism, and neurodegenerative diseases such as Parkinson's disease and Alzheimer's disease.

BACKGROUND OF THE INVENTION

Motor neuron diseases (MNDs) are an etiologically heterogeneous group of disorders that are characterized by muscle weakness and/or spastic paralysis, which results from the selective degeneration of lower motor neurons and/or upper motor neurons, respectively.

The MNDs currently being investigated are: amyotrophic lateral sclerosis (ALS), hereditary spastic paraplegia (HSP), primary lateral sclerosis (PLS), spinal muscular atrophy (SMA), spinal bulbar muscular atrophy (SBMA) and lethal congenital contracture syndrome (LCCS), while ALS is the most common adult-onset of the MNDs. Some examples of central disorders include cerebrovascular accident, Parkinson's disease, multiple sclerosis, Huntington's disease and Creutzfeldt-Jakob disease. Spinal muscular atrophies are disorders of lower motor neuron while amyotrophic lateral sclerosis (ALS) is a mixed upper and lower motor neuron condition, see Dion, P. A., Daoud, H., & Rouleau, G. A. (2009). Genetics of motor neuron disorders: new insights into pathogenic mechanisms. *Nature Reviews Genetics*, 10(11), 769, incorporated herein as reference.

ALS, provided herein as an example of the MNDs, is a neurodegenerative disease marked by neurodegeneration of both upper and lower motor neurons and progressive muscle impairment, atrophy and death within approximately five years from diagnosis.

Clinically indistinguishable forms of ALS occur as sporadic disease in the absence of known mutation, or can be initiated by genetic mutations. About two-third of familial cases are triggered by mutations of four genes that are chromosome 9 open reading frame 72 (C9ORF72), Cu/Zn superoxide dismutase (SOD1), fused in sarcoma/translocated in liposarcoma (FUS/TLS), TAR-DNA binding protein 43 (TDP43), see Volonté, C., Apolloni, S., & Parisi, C. (205). MicroRNAs: newcomers into the ALS picture. *CNS & Neurological Disorders-Drug Targets (Formerly Current Drug Targets-CNS & Neurological Disorders)*, 14(2), 194-207, incorporated herein as a reference.

Frontotemporal dementia (FTD) is a neurodegenerative condition which is characterized by progressive neuronal loss predominantly involving the frontal and/or temporal lobes, and typical loss of over 70% of spindle neurons, while other neuron types remain intact. Several recent findings have provided notable insights into the pathogenesis of amyotrophic lateral sclerosis (ALS), and have revealed mechanistic links between ALS and FTD, as well as between ALS and other neurodegenerative diseases, such as the cerebellar atrophies, myotonic dystrophy and inclusion body myositis, see Robberecht, Wim, and Thomas Philips. "The changing scene of amyotrophic lateral sclerosis." *Nature Reviews Neuroscience* 14.4 (2013): 248 incorporated herein as reference.

The etiology of ALS is still not clear. Some etiological factors include involvement of inflammation, and of MicroRNAs, as detailed in the following sections.

Inflammation: Animal and pathological studies suggest that inflammation may contribute to ALS pathology and that non-steroidal anti-inflammatory drugs (NSAIDs) might be protective A typical characteristic of ALS is neuroinflammation. Neuroinflammation is promoted by cyclooxygenase-2 (COX-2), and the activity of COX-2 can be inhibited by non-steroidal anti-inflammatory drugs (NSAIDs). NSAIDs have prolonged survival in transgenic mouse models of ALS, but results from a clinical trial did not find a protective effect of the selective COX-2 inhibitor Celecoxib on ALS disease progression (see Cudkowicz M E, et al (2006). Trial of celecoxib in amyotrophic lateral sclerosis. *Ann Neurol.;* 60:22-31, incorporated herein as a reference). Additionally, assessing whether NSAID use before symptom onset can reduce risk or delay the onset of ALS, by a case-control study on NSAID use and ALS (n=111 cases) yielded inconclusive results, see Popat R A, et al. (2007), *Effect of non-steroidal anti-inflammatory medications on the risk of amyotrophic lateral sclerosis. Amyotroph Lateral Scler.;* 8:157-63, and see Fondell, Elinor et al. *"Non-Steroidal Anti-Inflammatory Drugs and Amyotrophic Lateral Sclerosis: Results from 5 Prospective Cohort Studies." Amyotrophic lateral sclerosis: official publication of the World Federation of Neurology Research Group on Motor Neuron Diseases* 13.6 (2012): 573-579, incorporated herein as a reference.

MicroRNAs: The cause of ALS is not known, as is the reason why it affects some people and not others. However expert consensus is that molecular alterations in different cells are involved in the development and progression of the disease. For example, motor neuron death is caused by a variety of cellular defects, including the processing of RNA molecules.

During normal aging or neurodegenerative diseases, neuronal survival and function depend on protein homeostasis, which is regulated by multiple mechanisms, including the microRNA (miRNA) pathway. MicroRNAs are a subset of endogenous, small, non-coding RNA molecules involved in the post-transcriptional regulation of eukaryotic gene expression. Produced as long primary transcripts, they are exported to the cytoplasm and further modified to obtain the mature miRNAs, with each step of their biogenesis being a potential step of regulation. Dysregulation in miRNA-related pathways in the central nervous system (CNS) is associated with severe neuronal injury and cell death, which can lead to the development of neurodegenerative disorders, such as amyotrophic lateral sclerosis (ALS), see Rinchetti, P., Rizzuti, M., Faravelli, I., & Corti, S. (2017). *MicroRNA*

*metabolism and Dysregulation in amyotrophic lateral sclerosis. Molecular neurobiology*, 1-14, incorporated herein as a reference.

Furthermore, in different cells types, the absence of DICER, a key miRNA processing enzyme, leads to neurodegeneration through cell-autonomous and non-cell-autonomous mechanisms. Loss of certain miRNAs also causes neurodegeneration in some model organisms. On the other hand, miRNA expression is misregulated in patients with different neurodegenerative diseases. Thus, the miRNA pathway appears to be essential in the pathogenesis of several age-dependent neurodegenerative conditions; however, our understanding of the underlying mechanism remains rudimentary. Gascon, E., & Gao, F.-B. (2012). *Cause or Effect: Misregulation of microRNA Pathways in Neurodegeneration. Frontiers in Neuroscience*, 6, 48, incorporated herein as a reference.

Loss of miRNA biogenesis has been shown to cause spinal motor neuron degeneration in vivo (H see Haramati, Sharon, et al. "*miRNA malfunction causes spinal motor neuron disease.*" *Proceedings of the National Academy of Sciences* 107.29 (2010): 13111-13116, incorporated herein as reference). Additionally, it was demonstrated that reduction in miRNA levels is a common molecular denominator for multiple forms of familial and sporadic human ALS and that enhancement of DICER activity by a small molecule, enoxacin, is beneficial in vivo in two independent ALS mouse models. See Emde, Anna et al. "*Dysregulated miRNA Biogenesis Downstream of Cellular Stress and ALS-causing Mutations: A New Mechanism for ALS.*" *The EMBO Journal* 34.21(2015): 2633-2651, incorporated herein as a reference Treatment: Patient management is largely mediated by symptomatic therapies, such as the use of muscle relaxants for spasticity and speech therapy for dysarthria, see Hardiman, O., et al (2017). *Amyotrophic lateral sclerosis. Nature Reviews Disease Primers*, 3, 17071, incorporated herein as a reference.

Riluzole treatment was approved in 1995 after clinical trials showed that it modestly slowed ALS progression. Twenty-two years passed before another agent, Edaravone, was approved by the FDA for the treatment of ALS. See Brooks, B. R., et al (2018). *Edaravone in the Treatment of Amyotrophic Lateral Sclerosis: Efficacy and Access to Therapy—A Roundtable Discussion. The American journal of managed care.* 24(9 Suppl), S175-S186, incorporated herein as a reference.

Age-related macular degeneration Age-related macular degeneration (AMD) is a principal cause of blindness in the United States and other industrialized nations. An estimated 10 million Americans are afflicted with AMD, which is comparable in scope to the 12 million living with cancer (Hayat et al., 2007) or the 5 million with Alzheimer's disease. The prevalence of AMD steadily increases with age, affecting 2% of the population at age 40, and one in four people by age 80.

There are two types of AMD, the "dry" and "wet" forms. Dry AMD is a chronic disease that usually causes some degree of visual impairment and sometimes progresses to severe blindness. In contrast, wet AMD affects only 10%-15% of AMD patients, emerges abruptly, and rapidly progresses to blindness if left untreated. Since AMD patients typically develop the dry form first, wet AMD occurs on a background of dry AMD; as such, dry AMD can be considered a risk factor or even precursor state for wet AMD In the early stages of AMD, which is asymptomatic, insoluble extracellular aggregates called drusen accumulate in the retina. The late stage of dry AMD, which is also known as geographic atrophy (GA), is characterized by scattered or confluent areas of degeneration of retinal pigment epithelium (RPE) cells and the overlying light-sensing retinal photoreceptors, which rely on the RPE for trophic support. The other late stage form of AMD, the wet form, is typified by choroidal neovascularization (CNV) wherein newly immature blood vessels grow toward the outer retina from the underlying choroid. These immature blood vessels leak fluid below or within the retina.

The miRNA-processing enzyme DICER1 is a key determinant of RPE cell health.

The DICER1 has a role in governing RPE cell health and function via several mechanisms, including its influence on inflammation and global (coding and noncoding) RNA expression. DICER1, a ribonuclease, was specifically reduced in the RPE of GA patient); moreover, this pathological decrease in DICER1 was accompanied by the aberrant overabundance of the noncoding Alu RNA, which is toxic to RPE cells, see Ambati, J., & Fowler, B. J. (2012). *Mechanisms of age-related macular degeneration. Neuron,* 75(1), 26-39, incorporated herein as a reference.

Additionally, in GA, which is associated with reduced expression of Dicer, Inhibition of Dicer leads to accumulation of Alu repeat RNAs of ~300-nt derived from short interspersed elements (SINEs). This accumulation is cytotoxic and triggers interferon-mediated, caspase 8-dependent apoptosis. Injection of Alu repeat RNA into mouse eyes generates GA. This condition is rescued by Dicer cleavage of Alu repeat RNAs, suggesting that Dicer-dependent degradation of the RNAs is critical for detoxification. Dicer processing of Alu repeat RNA prevents activation of the host inflammasome. The DR2 Alu repeat RNAs are processed into 28-65-nt repeat-induced small RNAs (riRNAs) under DCIER-dependent conditions. These riRNAs are stabilized by binding with AGO3 and recruit mRNA-decapping complexes, which block translation and degrade key stem cell transcripts like Nanog and Tdgf1 mRNAs, see Song, M. S., & Rossi, J. J. (2017). *Molecular mechanisms of Dicer: endonuclease and enzymatic activity. Biochemical Journal,* 474(10), 1603-1618, incorporated herein as a reference.

The rarity of the ALS disease, along with the significant inter- and intra-patient variability in clinical course and a lack of reliable biomarkers, have rendered the development of effective agents to treat ALS a challenge. The need for a safe and effective treatment for ALS is still unmet.

Treatment of AMD is also largely an unmet need: Age-related macular degeneration (AMD) is a significant cause of global visual morbidity and is projected to affect 288 million people by the year 2040. The advent of treatment with anti-vascular endothelial growth factor (anti-VEGF) drugs has revolutionized the treatment of neovascular AMD (but there have been no similar breakthroughs for the treatment of geographic atrophy (GA) to retard its progression. The advancements in imaging and new understanding of disease mechanisms, based on molecular and genetic models, have paved the way for the development of novel experimental treatment options for GA that aim to cater to a thus far largely unmet need, see Kandasamy, R, Wickremasinghe, S., & Guymer, R. (2017). *New Treatment Modalities for Geographic Atrophy. Asia-Pacific journal of ophthalmology* (Philadelphia, Pa.), 6(6), 508-513, incorporated herein as reference.

SUMMARY OF THE INVENTION

The present invention relates to methods and compositions of an anti-inflammatory drug and a DICER activator for treatment of clinical indications. neuronal diseases including Motor neuron diseases (MNDs), ALS, FTD (Frontotemporal Dementia), macular degeneration (AMD) and autism.

As used herein after, the term "clinical indications" generally refers hereinafter to neuronal diseases.

As used herein after, the term "neuronal diseases" generally refers hereinafter to Motor neuron diseases (MNDs), FTD (Frontotemporal Dementia), macular degeneration (AMD), Alzheimer's disease, Parkinson's disease and autism.

As used herein after, the term "motor neuron diseases" or "MNDs" generally refers hereinafter to a group of diseases comprising, inter alia, amyotrophic lateral sclerosis (ALS), hereditary spastic paraplegia (HSP), primary lateral sclerosis (PLS), spinal muscular atrophy (SMA), spinal bulbar muscular atrophy (SBMA) and lethal congenital contracture syndrome (LCCS).

As used herein after, the term "anti-inflammatory drugs" "generally refers hereinafter, in a non-limiting matter, to a group of drugs comprising, inter ala steroids, corticosteroids or non-steroidal anti-inflammatory drugs (NSAIDs).

As used herein after, the term "Cyclooxygenase" or "COX", generally refers hereinafter to an enzyme (specifically, a family of isozymes) that is responsible for formation of prostanoids, including thromboxane and prostaglandins such as prostacyclin, from arachidonic acid. The main COX inhibitors are the non-steroidal anti-inflammatory drugs (NSAIDs).

As used herein after, the term "low dose" refers to a therapeutically effective dose of an anti-inflammatory drug, which dose is less than the usual or the conventional dose required to produce the therapeutic effect.

The classical COX inhibitors are not selective and inhibit all types of COX. The resulting inhibition of prostaglandin and thromboxane synthesis has the effect of reduced inflammation, as well as antipyretic, antithrombotic and analgesic effects.

As used herein after, the term "non-steroidal anti-inflammatory drugs" or "NSAIDs" generally refers hereinafter to a group of drugs comprising, inter ala COX-2 inhibitor, COX-1 inhibitors, COX inhibitors, aspirin, celecoxib diclofenac, diflunisal, etodolac, ibuprofen, indomethacin, ketoprofen, ketorolac, nabumetone, naproxen meloxicam, mefenamic acid meclofenamate, oxaprozin, piroxicam, salsalate, sulindac fenoprofen, flurbiprofen, and tolmetin.

As used herein after, the term "DICER" generally refers hereinafter to an enzyme that cleaves double-stranded RNA (dsRNA) and pre-microRNA (pre-miRNA) into short double-stranded RNA fragments called small interfering RNA and microRNA, respectively. These fragments are approximately 20-25 base pairs long with a two-base overhang on the 3' end. Dicer facilitates the activation of the RNA-induced silencing complex (RISC), which is essential for RNA interference. RISC has a catalytic component argonaute, which is an endonuclease capable of degrading messenger RNA (mRNA).

It is one object of the invention method for treating neuronal clinical indications in a mammalian subject wherein the method comprising administrating a combination of an anti-inflammatory drug and a DICER activator.

It is another object of the invention to disclose the method as defined in any of the above wherein the clinical indication is a neuronal disease.

It is one object of the invention to disclose a composition for treating neuronal clinical indications in a mammalian subject, wherein the composition comprises a synergistic combination of an anti-inflammatory drug and a DICER activator.

It is another object of the invention to disclose the composition as defined in any of the above wherein the clinical indication is a neuronal disease.

It is another object of the invention to disclose the composition as defined in any of the above wherein the clinical indication is a motor-neuron diseases (MND).

It is another object of the invention to disclose the composition as defined in any of the above wherein the clinical indication is autism.

It is another object of the invention to disclose the composition as defined in any of the above wherein the clinical indication is macular degeneration.

It is another object of the invention to disclose the composition as defined in any of the above wherein the clinical indication is axonopathy of motor neurons.

It is another object of the invention to disclose the composition as defined in any of the above wherein the clinical indication is a locomotor deficit.

It is another object of the invention to disclose the composition as defined in any of the above wherein the clinical indication is Parkinson's disease.

It is another object of the invention to disclose the composition as defined in any of the above wherein the clinical indication is Alzheimer's disease.

It is another object of the invention to disclose the composition as defined in any of the above wherein the inflammatory drug is a non-steroidal anti-inflammatory drug (NSAID).

It is another object of the invention to disclose the composition as defined in any of the above wherein the NSAID is a COX-2 inhibitor.

It is another object of the invention to disclose the composition as defined in any of the above wherein the NSAID is celecoxib.

It is another object of the invention to disclose the composition as defined in any of the above wherein the DICER activator is ciprofloxacin.

It is another object of the invention to disclose the composition as defined in any of the above wherein the DICER activator is ciprofloxacin-HCl.

It is another object of the invention to disclose the composition as defined in any of the above wherein the DICER activator is enoxacin.

It is another object of the invention to disclose the composition as defined in any of the above wherein the motor neuron diseases is selected from a group consisting one of amyotrophic lateral sclerosis (ALS), hereditary spastic paraplegia (HSP), primary lateral sclerosis (PLS), spinal muscular atrophy (SMA), spinal bulbar muscular atrophy (SBMA) and lethal congenital contracture syndrome (LCCS), and any combination thereof.

It is another object of the invention to disclose the composition as defined in any of the above wherein the anti-inflammatory drug to DICER activator ratio ranges from about 10:1 to about 1:1000 (wt/wt).

It is another object of the invention to disclose the composition as defined in any of the above wherein the anti-inflammatory drug to DICER activator ratio ranges from about 100:1 to about 1:1000 (wt/wt).

It is another object of the invention to disclose the composition as defined in any of the above wherein the anti-inflammatory drug to DICER activator ratio ranges from about 1:1 to about 1:200.

It is another object of the invention to disclose the composition as defined in any of the above wherein the anti-inflammatory drug to DICER activator ratio ranges from about 1:1 to about 1:50.

It is another object of the invention to disclose the composition as defined in any of the above wherein the anti-inflammatory drug to DICER activator ratio ranges from about 1:1 to about 1:10.

It is another object of the invention to disclose the composition as defined in any of the above wherein the anti-inflammatory drug to DICER activator ratio ranges from about 1:10 to about 1:200.

It is another object of the invention to disclose the composition as defined in any of the above wherein the anti-inflammatory drug to DICER activator ratio ranges from about 1:10 to about 1:50.

It is another object of the invention to disclose the composition as defined in any of the above wherein the anti-inflammatory drug to DICER activator ratio ranges from about 10:1 to about 1:1.

It is another object of the invention to disclose the composition as defined in any of the above wherein the anti-inflammatory drug is administered in a dose lower than indicated for anti-inflammatory clinical effect.

It is another object of the invention to disclose the composition as defined in any of the above wherein the celecoxib dose for human is ranging from about 10 mg to about 800 mg daily, and said ciprofloxacin dose for human is ranging from about 50 mg to about 2000 mg daily.

It is another object of the invention to disclose the composition as defined in any of the above wherein the anti-inflammatory drug is selected from a group consisting of steroids, corticosteroids or NSAIDs.

It is another object of the invention to disclose the composition as defined in any of the above wherein the DICER activator is a quinolone or a fluoroquinolone.

It is another object of the invention to disclose the composition as defined in any of the above wherein the quinolone is selected from a group consisting of 2-quinolone, 4-quinolone, fluoroquinolones, lomefloxacin, ofloxacin, norfloxacin, gatifloxacin, ciprofloxacin, levofloxacin, ciprofloxacin, gemifloxacin, delafloxacin, cinoxacin, nalidixic acid, trovafloxacin, sparfloxacin, and any combination thereof.

It is another object of the invention to disclose the composition as defined in any of the above wherein the NSAID is selected from a group consisting of COX-2 inhibitor, COX-1 inhibitors, COX inhibitors, aspirin, celecoxib diclofenac, diflunisal, etodolac, ibuprofen, indomethacin, ketoprofen, ketorolac, nabumetone, naproxen meloxicam, mefenamic acid meclofenamate, oxaprozin, piroxicam, salsalate, sulindac fenoprofen, flurbiprofen, tolmetin and any combination thereof.

It is another object of the invention to disclose the composition as defined in any of the above wherein the composition is configured to be administrable in a manner selected from a group consisting of a tablet, a capsule, a pill, lyophilized, powder, emulsion, granulated powder, cream, ointment, paste, lotion gel, liquid, a solution, a patch and any combination thereof.

It is another object of the invention to disclose the composition as defined in any of the above wherein the composition is configured to be administrable in a manner selected from a group consisting of fast release, slow release, sustained release, controlled release and any combination thereof.

It is another object of the invention to disclose the composition as defined in any of the above wherein the composition additionally comprising ingredients selected from a group consisting solubilizers, stabilizers, buffers, tonicity modifiers, bulking agents, viscosity enhancers/reducers, surfactants, chelating agents, adjuvants and any combination thereof.

It is one object of the invention to disclose a kit for a synergistic treatment of neuronal clinical indications in a mammalian subject wherein the kit comprising both of an anti-inflammatory drug and a DICER activator.

It is another object of the invention to disclose the kit for a synergistic treatment of neuronal clinical indications in a mammalian subject wherein the kit comprising a dosage unit comprising both: an anti-inflammatory drug and a DICER activator.

It is one object of the invention to disclose a method for treating neuronal clinical indications in a mammalian subject wherein the method comprising administrating a synergistic combination of an anti-inflammatory drug and a DICER activator.

It is another object of the invention to disclose the method as defined in any of the above wherein the clinical indication is a neuronal disease.

It is another object of the invention to disclose the method as defined in any of the above wherein the clinical indication is a motor-neuron diseases (MND).

It is another object of the invention to disclose the method as defined in any of the above wherein the clinical indication is autism.

It is another object of the invention to disclose the method as defined in any of the above wherein the clinical indication is macular degeneration.

It is another object of the invention to disclose the method as defined in any of the above wherein the clinical indication is axonopathy of motor neurons.

It is another object of the invention to disclose the method as defined in any of the above wherein the clinical indication is a locomotor deficit.

It is another object of the invention to disclose the method as defined in any of the above wherein the clinical indication is Parkinson's disease.

It is another object of the invention to disclose the method as defined in any of the above wherein the clinical indication is Alzheimer's disease.

It is another object of the invention to disclose the method as defined in any of the above wherein the inflammatory drug is a non-steroidal anti-inflammatory drug (NSAID).

It is another object of the invention to disclose the method as defined in any of the above wherein the NSAID is a COX-2 inhibitor.

It is another object of the invention to disclose the method as defined in any of the above wherein the NSAID is celecoxib.

It is another object of the invention to disclose the method as defined in any of the above wherein the DICER activator is ciprofloxacin.

It is another object of the invention to disclose the method as defined in any of the above wherein the DICER activator is ciprofloxacin-HCl.

It is another object of the invention to disclose the method as defined in any of the above wherein the DICER activator is enoxacin.

It is another object of the invention to disclose the method as defined in any of the above wherein the motor neuron diseases is selected from a group consisting one of amyotrophic lateral sclerosis (ALS), hereditary spastic paraplegia (HSP), primary lateral sclerosis (PLS), spinal muscular atrophy (SMA), spinal bulbar muscular atrophy (SBMA) and lethal congenital contracture syndrome (LCCS), and any combination thereof.

It is another object of the invention to disclose the method as defined in any of the above wherein the anti-inflammatory drug to DICER activator ratio ranges from about 10:1 to about 1:1000 (wt/wt).

It is another object of the invention to disclose the method as defined in any of the above wherein the anti-inflammatory drug to DICER activator ratio ranges from about 100:1 to about 1:1000 (wt/wt).

It is another object of the invention to disclose the method as defined in any of the above wherein the anti-inflammatory drug to DICER activator ratio ranges from about 1:1 to about 1:200.

It is another object of the invention to disclose the method as defined in any of the above wherein the anti-inflammatory drug to DICER activator ratio ranges from about 1:1 to about 1:50.

It is another object of the invention to disclose the method as defined in any of the above wherein the anti-inflammatory drug to DICER activator ratio ranges from about 1:1 to about 1:10.

It is another object of the invention to disclose the method as defined in any of the above wherein the anti-inflammatory drug to DICER activator ratio ranges from about 1:10 to about 1:200.

It is another object of the invention to disclose the method as defined in any of the above wherein the anti-inflammatory drug to DICER activator ratio ranges from about 1:10 to about 1:50.

It is another object of the invention to disclose the method as defined in any of the above wherein the anti-inflammatory drug to DICER activator ratio ranges from about 10:1 to about 1:1.

It is another object of the invention to disclose the method as defined in any of the above wherein the anti-inflammatory drug is administered in a dose lower than indicated for anti-inflammatory clinical effect.

It is another object of the invention to disclose the method as defined in any of the above wherein the celecoxib dose for human is ranging from about 10 mg to about 800 mg daily, and said ciprofloxacin dose for human is ranging from about 50 mg to about 2000 mg daily.

It is another object of the invention to disclose the method as defined in any of the above wherein the anti-inflammatory drug is selected from a group consisting of steroids, corticosteroids or NSAIDs.

It is another object of the invention to disclose the method as defined in any of the above wherein the DICER activator is a quinolone or a fluoroquinolone It is another object of the invention to disclose the method as defined in any of the above wherein the quinolone is selected from a group consisting of 2-quinolone, 4-quinolone, fluoroquinolones, lomefloxacin, ofloxacin, norfloxacin, gatifloxacin, ciprofloxacin, levofloxacin, ciprofloxacin, gemifloxacin, delafloxacin, cinoxacin, nalidixic acid, trovafloxacin, sparfloxacin, and any combination thereof.

It is another object of the invention to disclose the method as defined in any of the above wherein the NSAID is selected from a group consisting of COX-2 inhibitor, COX-1 inhibitors, COX inhibitors, aspirin, celecoxib diclofenac, diflunisal, etodolac, ibuprofen, indomethacin, ketoprofen, ketorolac, nabumetone, naproxen meloxicam, mefenamic acid meclofenamate, oxaprozin, piroxicam, salsalate, sulindac fenoprofen, flurbiprofen, tolmetin and any combination thereof.

It is another object of the invention to disclose the method as defined in any of the above wherein the method comprising administrating synergistic combination of an anti-inflammatory drug and a DICER activator in a manner selected from a group consisting of oral, topical, dermal, transdermal, intravenous, subcutaneous, intramuscular, intra-articular, suppository, intraventricular, inhalational, aerosol, sublingual and any combination thereof.

It is another object of the invention to disclose the method as defined in any of the above wherein the method comprising administrating synergistic combination of an anti-inflammatory drug and a DICER activator in a manner selected from a group consisting of fast release, slow release, sustained release, controlled release and any combination thereof.

It is another object of the invention to disclose the method as defined in any of the above wherein the method comprising administrating synergistic combination of an anti-inflammatory drug and a DICER activator in a manner selected from a group consisting of one at a time, non-simultaneous, sequentially and concomitantly.

It is another object of the invention to disclose the method as defined in any of the above wherein the method comprising administrating synergistic combination of an anti-inflammatory drug and a DICER activator in a manner selected from a group consisting of single dose, single daily dose, twice daily dose, continuous dose, infusion, and any combination thereof.

It is another object of the invention to disclose the method as defined in any of the above wherein the composition is selected from a group consisting of a tablet, a capsule, a pill, lyophilized, powder, emulsion, granulated powder, cream, ointment, paste, lotion gel, liquid, a solution, a patch and any combination thereof.

It is another object of the invention to disclose the method as defined in any of the above wherein the composition additionally comprising ingredients selected from a group consisting solubilizers, stabilizers, buffers, tonicity modifiers, bulking agents, viscosity enhancers/reducers, surfactants, chelating agents, adjuvants and any combination thereof.

BRIEF DESCRIPTION OF THE DRAWINGS

The present invention will hereinafter be described in conjunction with the following drawing figures.

DETAILED DESCRIPTION OF PREFERRED EMBODIMENTS

Figure 1:
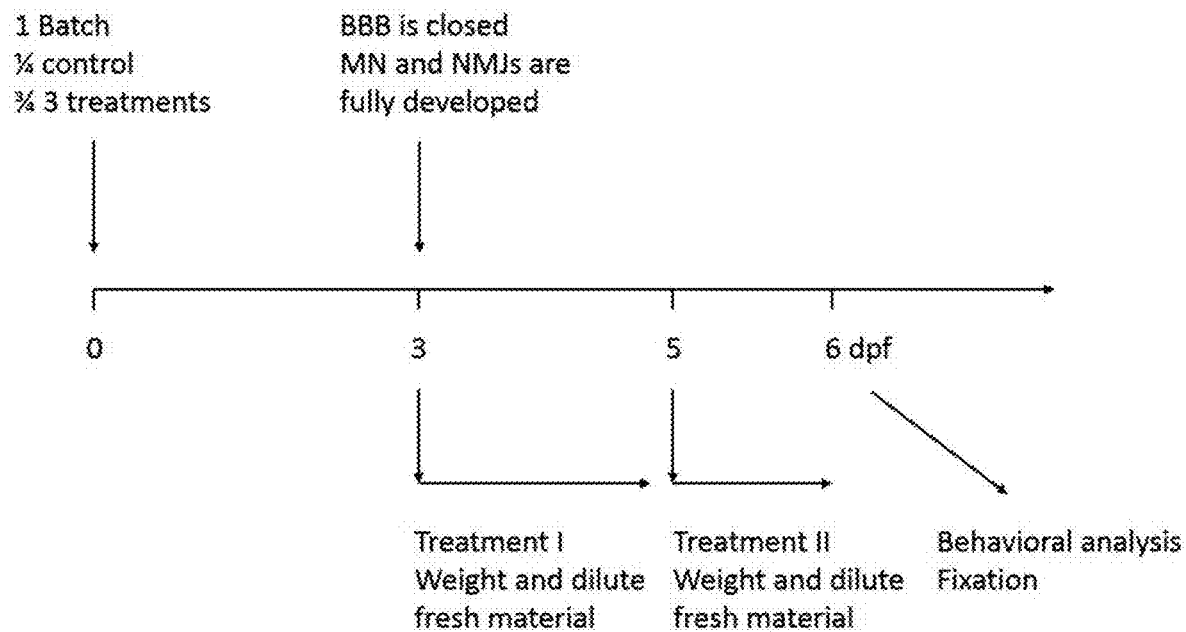
FIG. 1: Scheme exhibiting the treatment protocol.

The present invention discloses a composition for treating neuronal diseases in a mammalian subject, wherein the composition comprises a combination of an anti-inflammatory drug and a DICER activator.

The present invention discloses therapeutic compositions and therapeutic methods thereof, for MNDs (including ALS) and frontotemporal dementia (FTD), aiming to present an effective treatment for patients diagnosed with an MND. The technology hereto presented underlines the role of miRNAs in addition to anti-inflammatory drug which has a neuroprotective effect in the development of ALS by using in vivo and in vitro pharmacological models of ALS, see Berthod, François, and François Gros-Louis. *"In vivo and in vitro models to stud amyotrophic lateral sclerosis." Amyotrophic Lateral Sclerosis. InTech,* 2012 which is incorporated herein as a reference.

The present invention discloses a combination of a quinolone, which is a DICER enhancer, and an anti-inflammatory agent, as a treatment.

A non-limiting example is ciprofloxacin as a quinolone, specifically a fluoroquinolone, which enhances Dicer activity and is therefore able to upregulate microRNA biogenesis, and celecoxib as a COX-2 selective nonsteroidal anti-inflammatory drug (NSAID).

The quinolones are broad-spectrum antibacterial agents that have a novel mechanism of action. As synthetic compounds, these agents have been developed extensively to optimize antimicrobial activity, pharmacokinetic properties, and drug safety. The quinolones have wide potential applications and a broader spectrum of activity. Ciprofloxacin remains the most potent quinolone against *Pseudomonas aeruginosa*, see Walker, R. C. (1999, October). *The fluoroquinolones. In Mayo Clinic Proceedings* (Vol. 74, No. 10, pp. 1030-1037), incorporated herein as a reference.

Quinolones cause synergistic or additive toxicity with NSAIDs. The concomitant administration of quinolones and nonsteroidal NSAIDs has reportedly led to increased CNS stimulation. The concomitant administration of quinolones and NSAIDs has been reported to increase the risk of CNS stimulation and convulsive seizures. Patients with CNS disorders or other risk factors that may predispose them to seizure development or patients taking drugs that lower the seizure threshold may not be appropriate candidates for NSAID usage if they are also taking a quinolone. Use a quinolone with caution in individuals who take a NSAID concomitantly.

As a consequence, the aforesaid teaching against prior art is hereby contradicted, for the present invention's novel claim that the combination of the two suggested drugs results in a positive, significant and surprising outcome to ALS patients, which don't have risk factors that may predispose them to seizure development, perhaps with a new formulation that extends the release of the drugs for a continues treatment.

Specifically, epileptogenic activity induced by combined treatment with anti-inflammatory drugs and enoxacin was investigated in chronic electrode-implanted rats. Ferubinac ethyl and aspirin DL-lysine showed a spike and wave complex in EEG without showing remarkable behavioral changes when they were injected intraventricularly, although a relatively high dose was needed. Enoxacin, on the other hand, elicited potent epileptogenic activity characterized by uninterrupted high voltage spike and wave complex at doses of 50 and 100 micrograms. At the same time, rats showed hyperactivity, jumping and violent convulsion. Combined treatment with enoxacin (p.o.) and ferubinac ethyl (i.v.) caused potent epileptogenic activity characterized by uninterrupted burst of high voltage spike and wave complex. Behaviorally, animals showed forelimb clonus, head nodding and generalized convulsion. High voltage spike and wave complex was also observed after combined treatment with enoxacin (i. vent.) and ferubinac ethyl (i.v. or i. vent.) in association with hyperactivity and jumping and violent convulsion). It is concluded that simultaneous treatment with enoxacin and ferubinac ethyl produced epileptogenic activity when injected intraventricularly, see Kamei, Chiaki, et al. "Epileptogenic activity induced by combined treatment with antiinflammatory drugs and enoxacin and its inhibition by a calcium antagonist, nicardipine." *Methods and findings in experimental and clinical pharmacology* 18.9 (1996): 579-588, incorporated herein as a reference.

The present invention used SOD1 G93R mutant and WT fish to assess the effect of anti-inflammatory agents and DICER activators compared to available treatments for ALS, (see FIG. 1 for treatment protocol).

Figure 2:
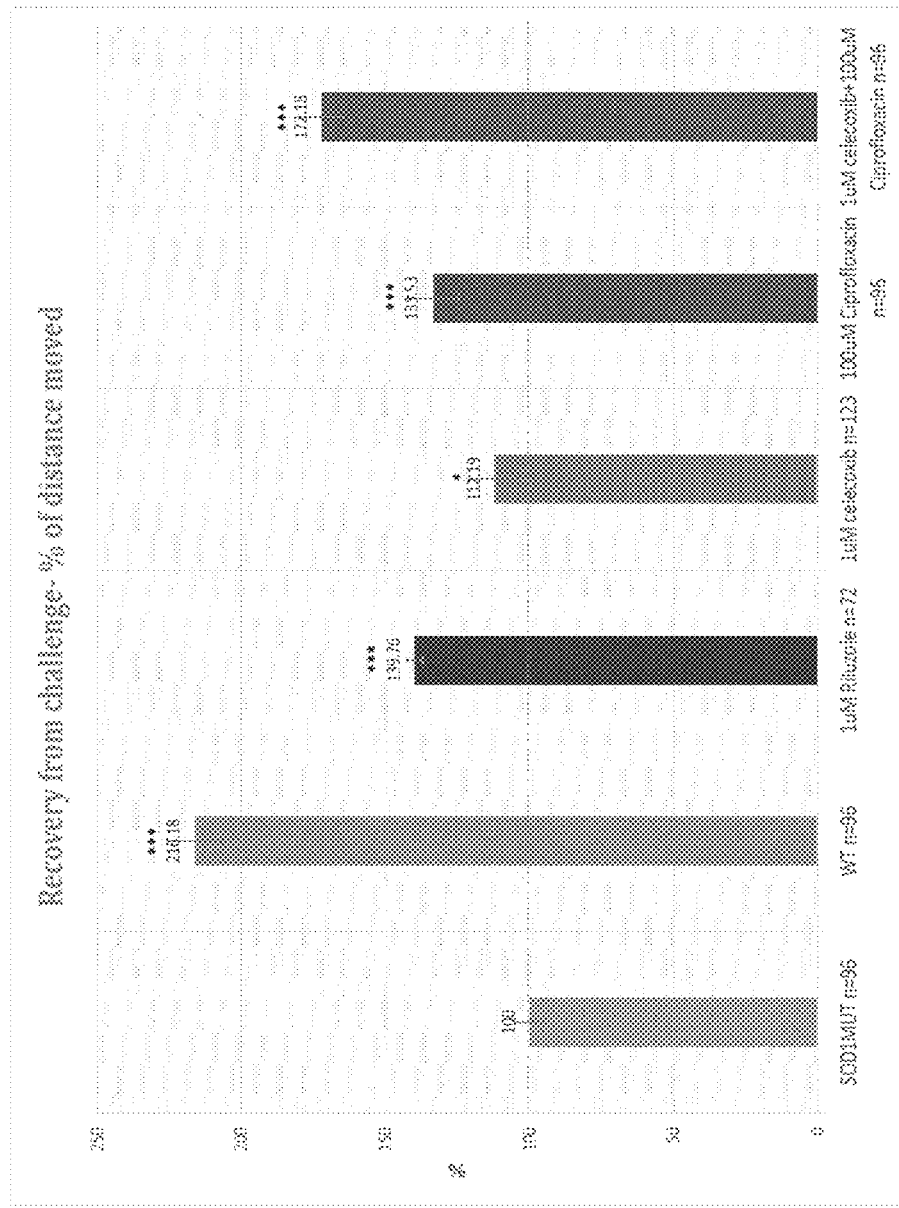
FIG. 2: The change in distance moved (in %) of non-treated SOD1 G93R compared to wild type and to the treated SOD1 larva in the recovery from challenge phase.
Figure 3:
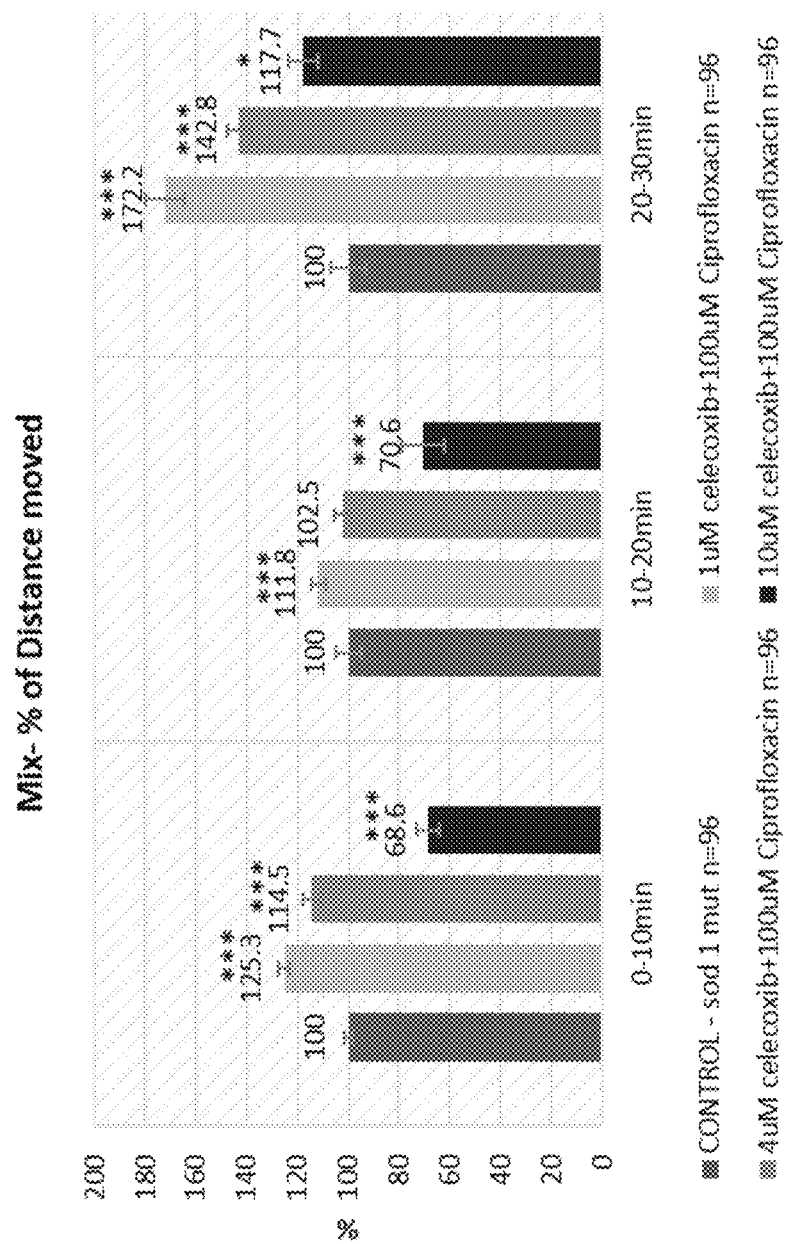
FIG. 3: Ciprofloxacin and Celecoxib combinations—treated SOD1 mutants' locomotor activity compared to non-treated SOD1 mutants in all 3 phases of the experiment.

The present invention recites a synergistic effect in SOD1 mutant fish treated with both Ciprofloxacin and Celecoxib, specifically at concentrations of 1 µM Celecoxib and 100

μM Ciprofloxacin. At these concentrations, there was a dramatic effect on their swimming ability compared to non-treated mutants (FIGS. 2, 3).

Figure 4:
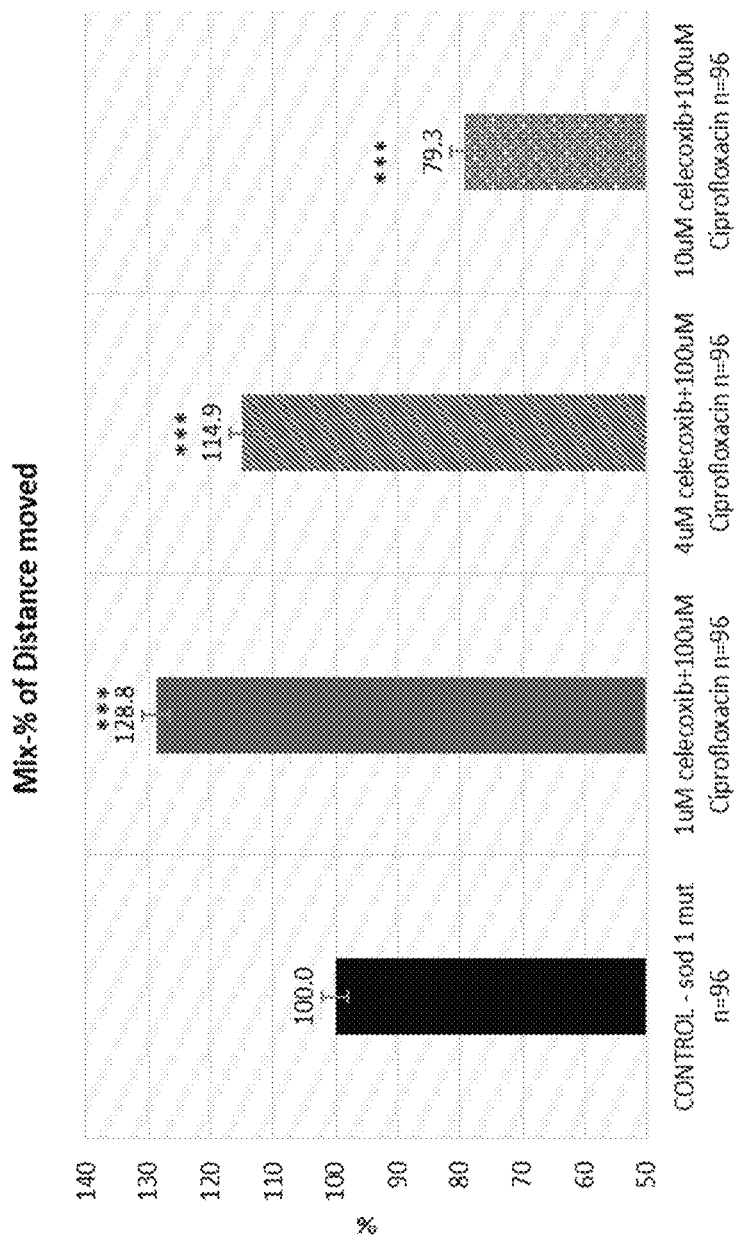
FIG. 4: Ciprofloxacin and Celecoxib combinations—treated SOD1 mutants' locomotor activity compared to non-treated SOD1 mutants during the whole period of measurement.
Figure 5:
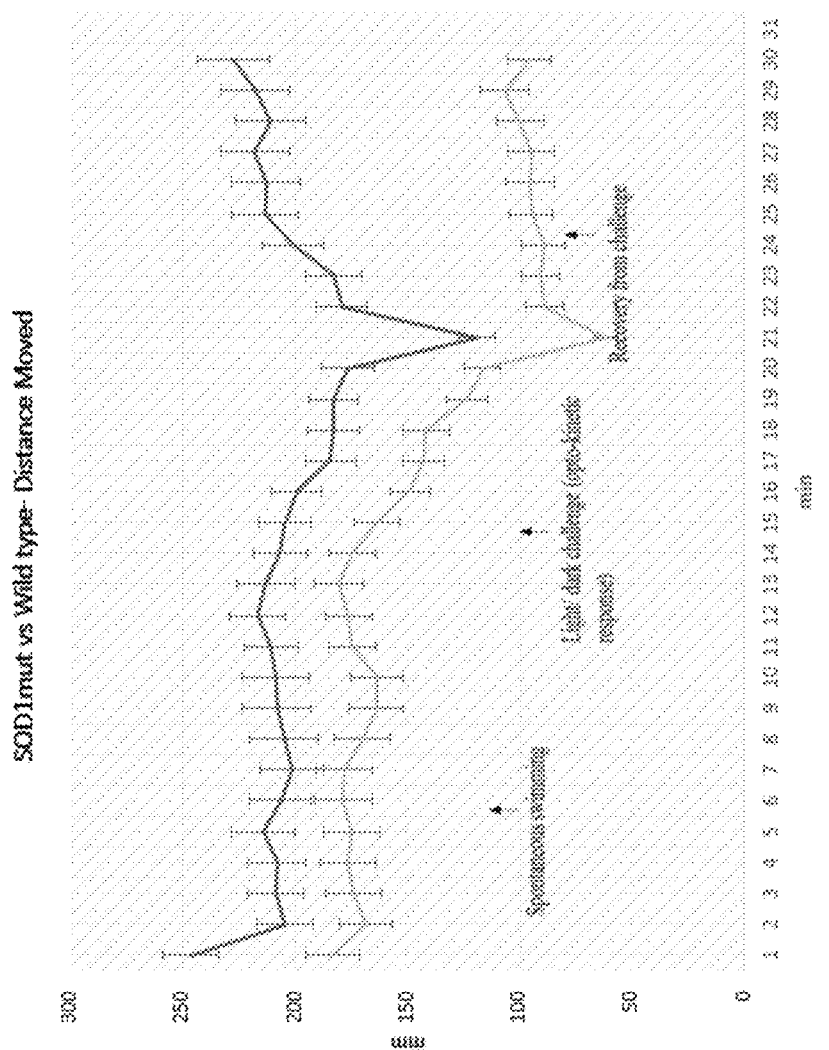
FIG. 5: The distance moved measured and calculated for 96 SOD1 mutant vs WT larvae per time bin of 1 minute.

The treated SOD1 mutant larva distance moved was elevated by 29% compared to non-treated SOD1 mutant swimming behavior (FIG. 4). The effect was striking enough that the treated SOD1 fish behavior closely resembled that of wild type fish (FIG. 5).

The combination of the present invention is in a ratio ranging from about 10:1 to about 1:1000, of an anti-inflammatory drug and a DICER activator. Specifically:

As used herein the term "about" refers to ±10%
a. The combination is in a ratio ranging from about 100:1 to about 1:1000, of an anti-inflammatory drug and a DICER activator.
b. The combination is in a ratio ranging from about 1:1 to about 1:200, of an anti-inflammatory drug and a DICER activator.
c. The combination is in a ratio ranging from about 1:1 to about 1:50, of an anti-inflammatory drug and a DICER activator.
d. The combination is in a ratio ranging from about 1:1 to about 1:10, of an anti-inflammatory drug and a DICER activator.
e. The combination is in a ratio ranging from about 1:10 to about 1:200, of an anti-inflammatory drug and a DICER activator.
f. The combination is in a ratio ranging from about 1:10 to about 1:50, of an anti-inflammatory drug and a DICER activator.
g. The combination is in a ratio ranging from about 10:1 to about 1:1, of an anti-inflammatory drug and a DICER activator.

EXAMPLE 1

Figure 6:
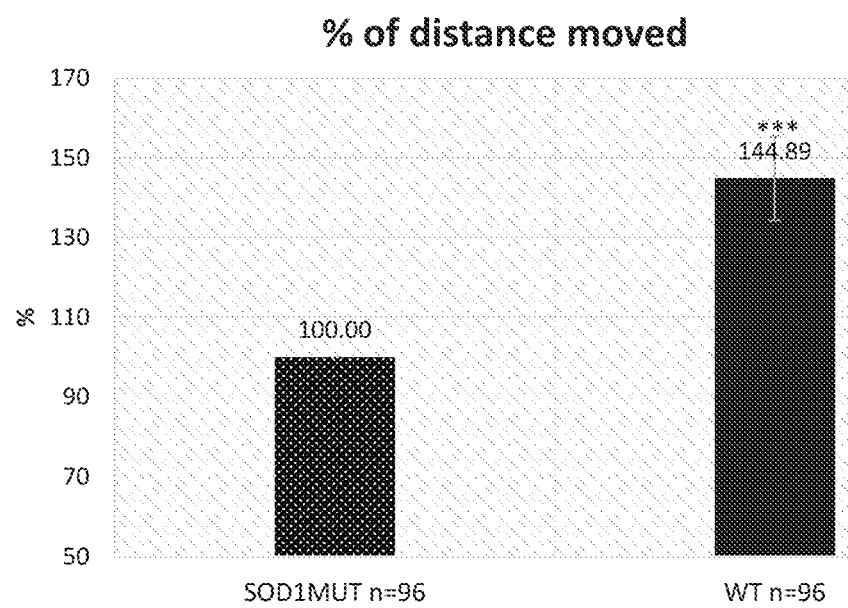
FIG. 6: SOD1 mutants displayed a significant reduction in their locomotor activity compared to WT during the whole period of measurement.
Figure 7:
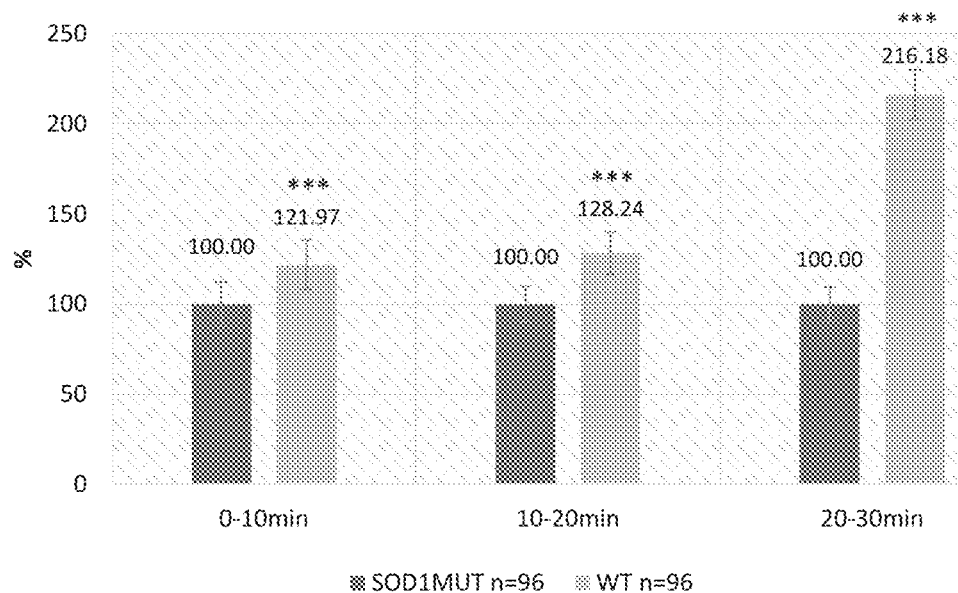
FIG. 7: SOD1 mutants displayed a significant reduction in their locomotor activity compared to WT in all 3 phases of the experiment.

Transgenic zebrafish for the top ALS-linked gene superoxide dismutase 1 (SOD1) were utilized in this study. It was previously shown that the SOD1 G93R mutant fish recapitulate the major phenotypes of ALS including neuromuscular junction defects, decreased endurance, motor neurons loss and muscle pathology, see Ramesh T, Lyon A N, Pineda R H, et al. A genetic model of amyotrophic lateral sclerosis in zebrafish displays phenotypic hallmarks of motoneuron disease. *Disease models & mechanisms* 2010; 3:652-62, incorporated herein as reference. SOD1 mutation caused behavioral deficits related to locomotion. The SOD1 mutant animals showed significant reduction in their swimming ability compared to the wild type during the spontaneous swimming, light/dark challenge and most dramatically following the second peak of stress, exhibiting recovery from the challenge (FIGS. 5-7). The distance the wild type larva moved was averaged for the whole period of time and was elevated by 44% compared to SOD1 mutant swimming behavior (FIG. 6).

Figure 8:
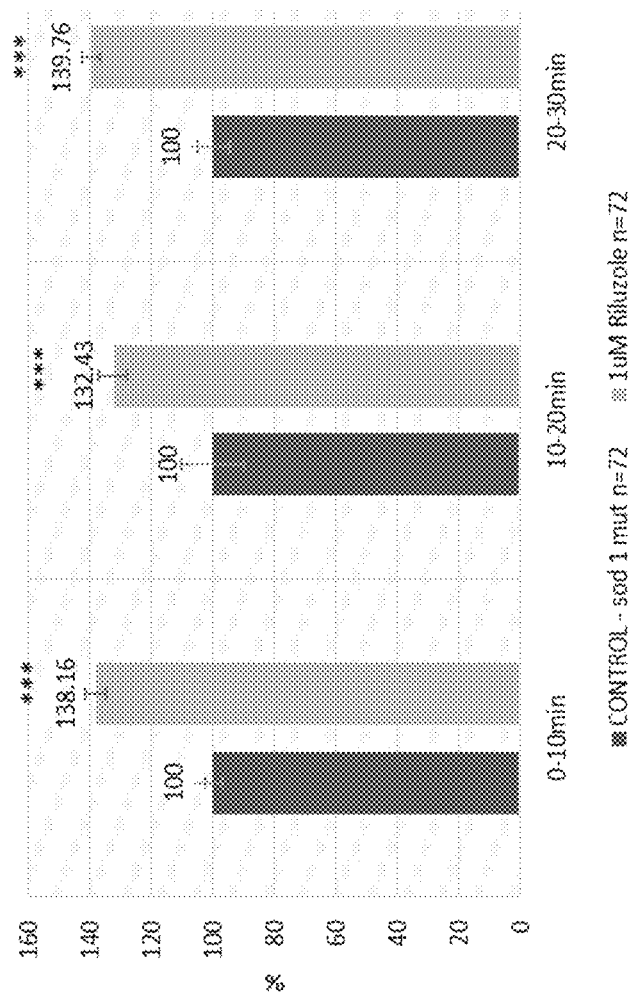
FIG. 8: Riluzole-treated SOD1 mutants displayed a significant elevation in their locomotor activity compared to non-treated Sod1 mutants in all 3 phases of the experiment.

As a positive control, the SOD1 mutant fish were treated with Riluzole (FIG. 8). Riluzole was chosen for this study as it was for years the only established drug shown to have a disease-modifying effect in ALS patients, see Bensimon G, Lacomblez L, Meininger V, Group tARS. *A Controlled Trial of Riluzole in Amyotrophic Lateral Sclerosis. New England Journal of Medicine* 1994; 330:585-91, incorporated herein as a reference. The SOD1 mutant animals treated with Riluzole showed significant elevation of 36% compared to SOD1 mutant swimming behavior.

Figure 9:
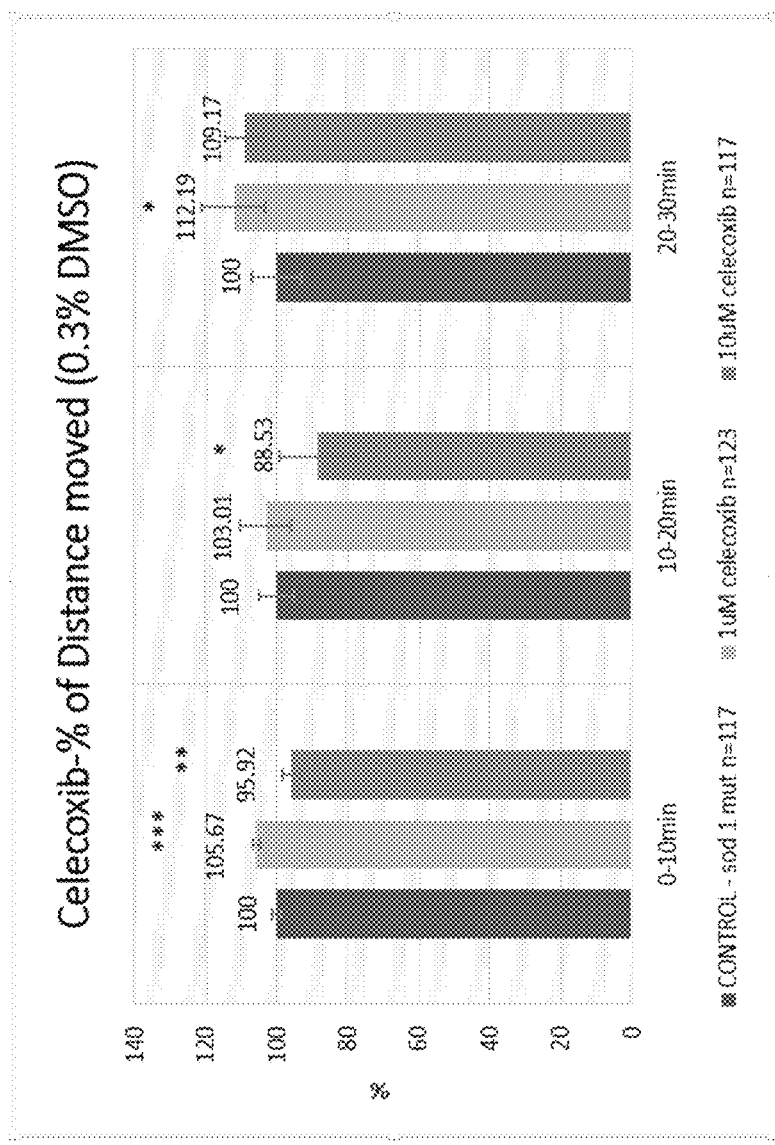
FIG. 9: Celecoxib-treated SOD1 mutants' locomotor activity compared to non-treated SOD1 mutants in all 3 phases of the experiment.

In the next series of experiments, SOD1 mutant fish were treated with Celecoxib at distinct concentrations (FIG. 9).

Toxicity of Celecoxib was noticeable in high concentrations (30 μM) in both SOD1 mutants and WT animals, including cardiovascular toxicity and death. Treatment of SOD1 mutant larvae with lower Celecoxib concentrations revealed subtle locomotor decline in 10 μM (with 0.3% DMSO background) and in 5 μM (with 0.1% DMSO as a background). Below these concentrations, no toxicity was evident and the overall morphology and behavior were normal. Importantly, our results show that Celecoxib toxicity is parallel in both ALS and healthy subjects and the SOD1 mutants do not show higher susceptibility to the drug (section III).

Figure 10:
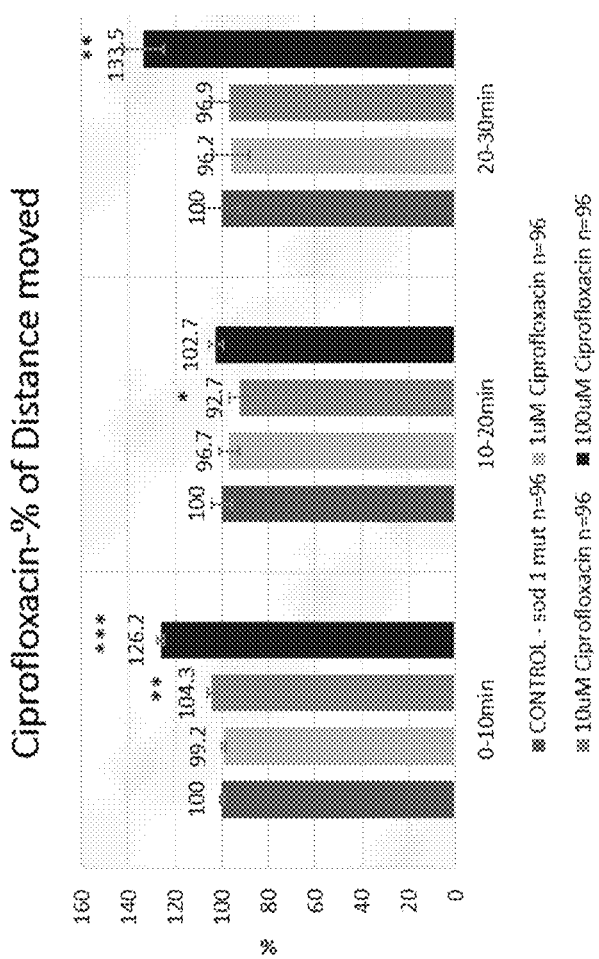
FIG. 10: Ciprofloxacin-treated SOD1 mutants' locomotor activity compared to non-treated SOD1 mutants in all 3 phases of the experiment.
Figure 14:
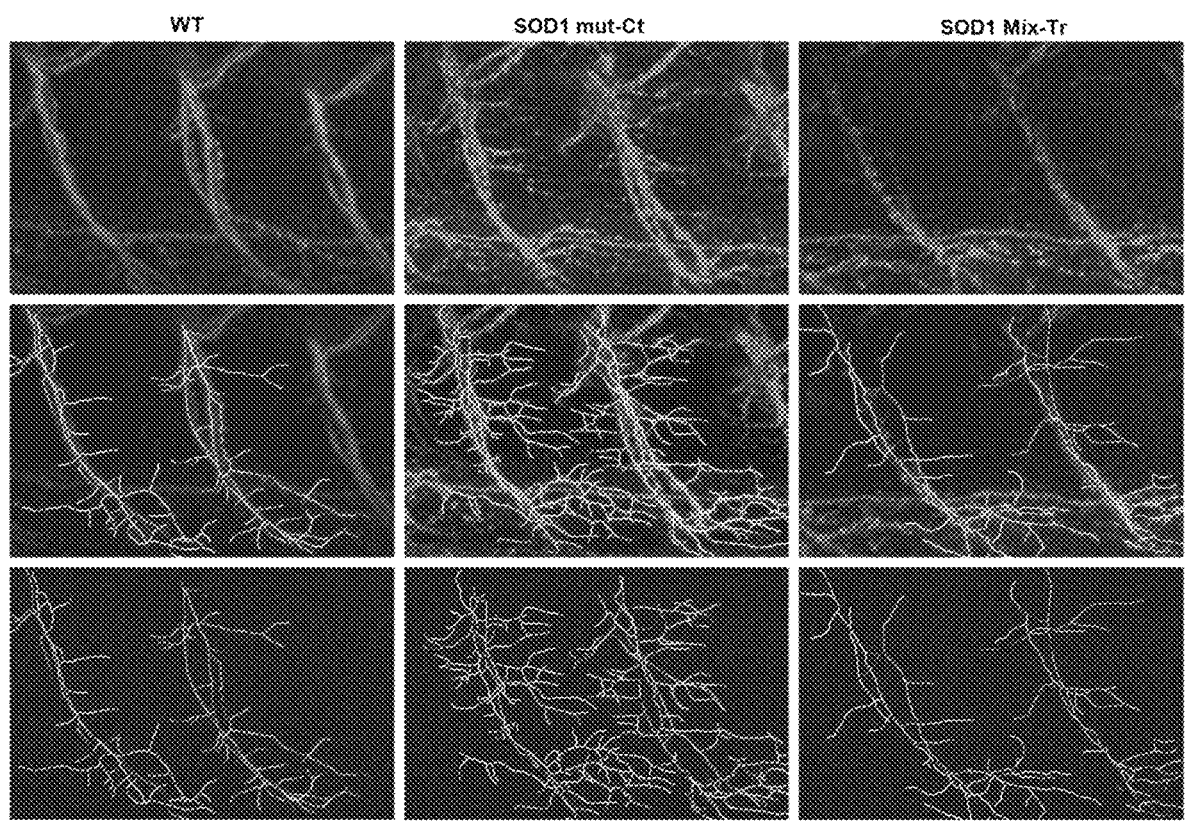
FIG. 14: Administration of Ciprofloxacin and Celecoxib recovered axonopathy of SOD1 mutant fish. Morphological analysis of individual motor neurons in the trunk of zebrafish larva; segments S10-S12 were used for analysis. Left panel—WT, middle panel—non-treated SOD1 mutant fish, left panel—1 µM Celecoxib+100 µM Ciprofloxacin-treated SOD1 mutant fish. Upper panel—3D reconstructed apotome z-stack images of branching motor neurons in the trunk of 6 dpf zebrafish larvae immunostained with anti-acetylated tubulin antibodies. Middle and lower panels—The backbone (colored processes) of motor neurons traced with the Filaments analysis of Imaris software (Bitplane; in yellow—single motor neuron backbone). n=15; control and treated SOD1 mutants and n=11; WT fish.

Overall, treatment at all doses did not strikingly improve swimming behavior. At 1 μM, there was a 6% increase in swimming activity as compared to untreated SOD1 mutant swimming behavior SOD1 mutant fish were then treated with Ciprofloxacin at concentrations of 500, 200, 100, 50, 10 and 1 μM (FIGS. 10, 14). All Ciprofloxacin doses were safe for the fish, showing no overall or subtle morphological and behavioral toxicity. The higher concentrations had a positive effect on SOD1 mutants' swimming ability with the 100 μM concentration showing the greatest benefit. At that level, SOD1 mutant larva distance moved was elevated by 18% compared to non-treated SOD1 mutant swimming behavior).

SOD1 mutant fish treated with Ciprofloxacin showed similarity to treatment with the same doses of Enoxacin, its family member (FIG. 10). Enoxacin-treated SOD1 mutant larva distance moved was elevated by 20% compared to non-treated SOD1 mutant swimming behavior.

Next, SOD1 mutant fish were treated with both Ciprofloxacin and Celecoxib at a variety of concentrations. The greatest effect was seen at concentrations of 1 μM Celecoxib and 100 μM Ciprofloxacin; at these concentrations, there was a dramatic effect on their swimming ability compared to non-treated mutants (FIG. 3). The treated SOD1 mutant larva distance moved was elevated by 29% compared to non-treated SOD1 mutant swimming behavior (FIG. 4). The effect was striking enough that the treated SOD1 fish behavior closely resembled that of wild type fish.

To summarize the distinct effects of the treatments on fish motor abilities, we averaged the last 10 minutes of the distance moved (FIG. 2). Following introduction of additional muscle and neurological stress, this recovery from challenge phase is aimed to identify enhanced muscle endurance. Wild type animals swam longer distances during this period compared to the SOD1 mutant fish (elevation of 116%). Riluzole induced a clear increase in the swimming abilities of the fish (39.7%), but significant synergistic effect was seen with the combination of Ciprofloxacin at 100 μM and celecoxib at 1 μM (72%, FIG. 2). FIG. 2 discloses the change in distance moved (in %) of non-treated SOD1 G93R compared to wild type and to the treated SOD1 larva in the recovery from challenge phase.

Figure 15A:
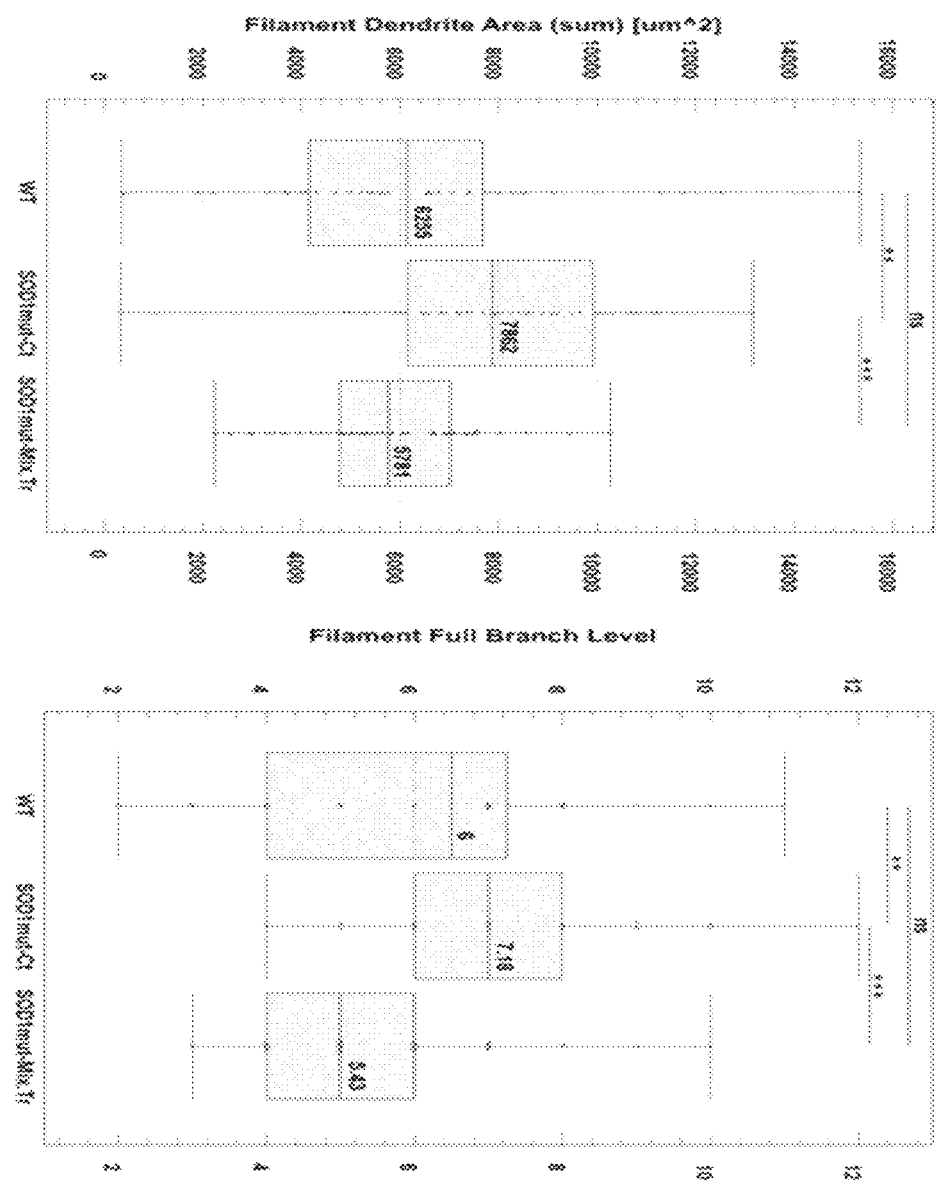
FIGS. 15A, 15B, 15C: Combination of Ciprofloxacin and Celecoxib caused a nearly full recovery of motor neurons axonopathy of SOD1 mutant fish. Aspects of length and branching of motor neurons axonal projections were calculated using the Imaris software (Bitplane) and are plotted in the graphs.
Figure 15B:
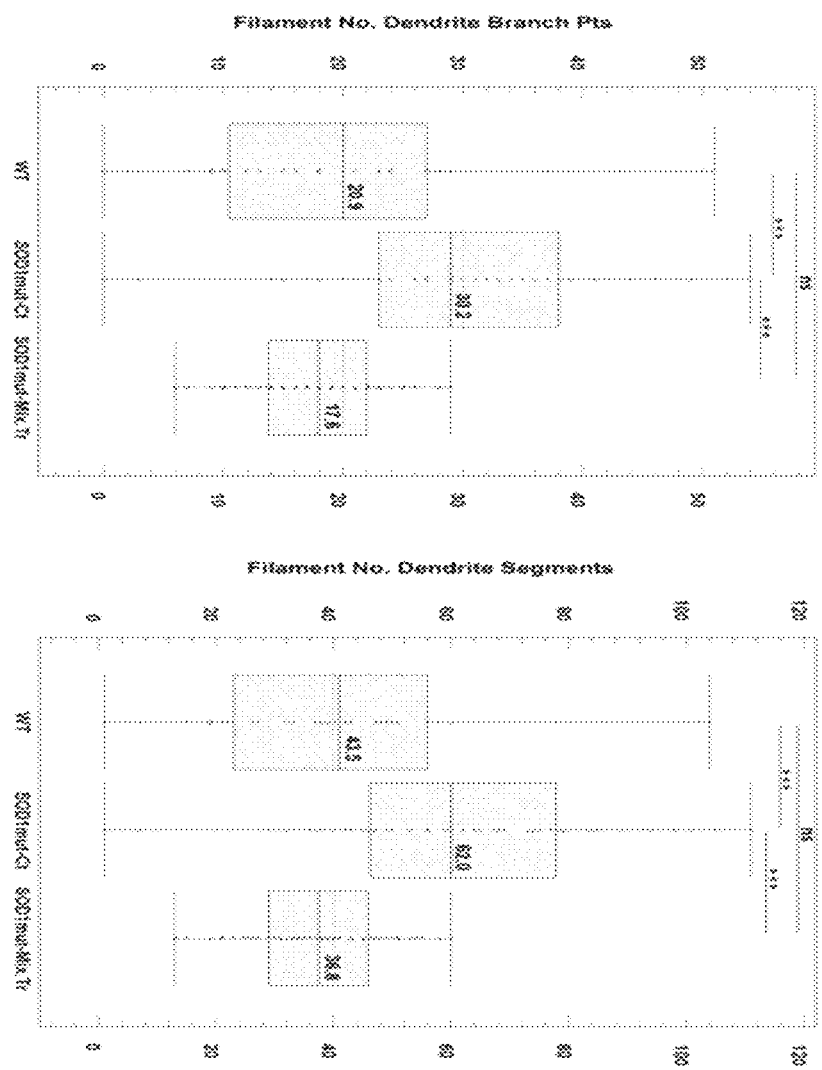
Figure 15C:
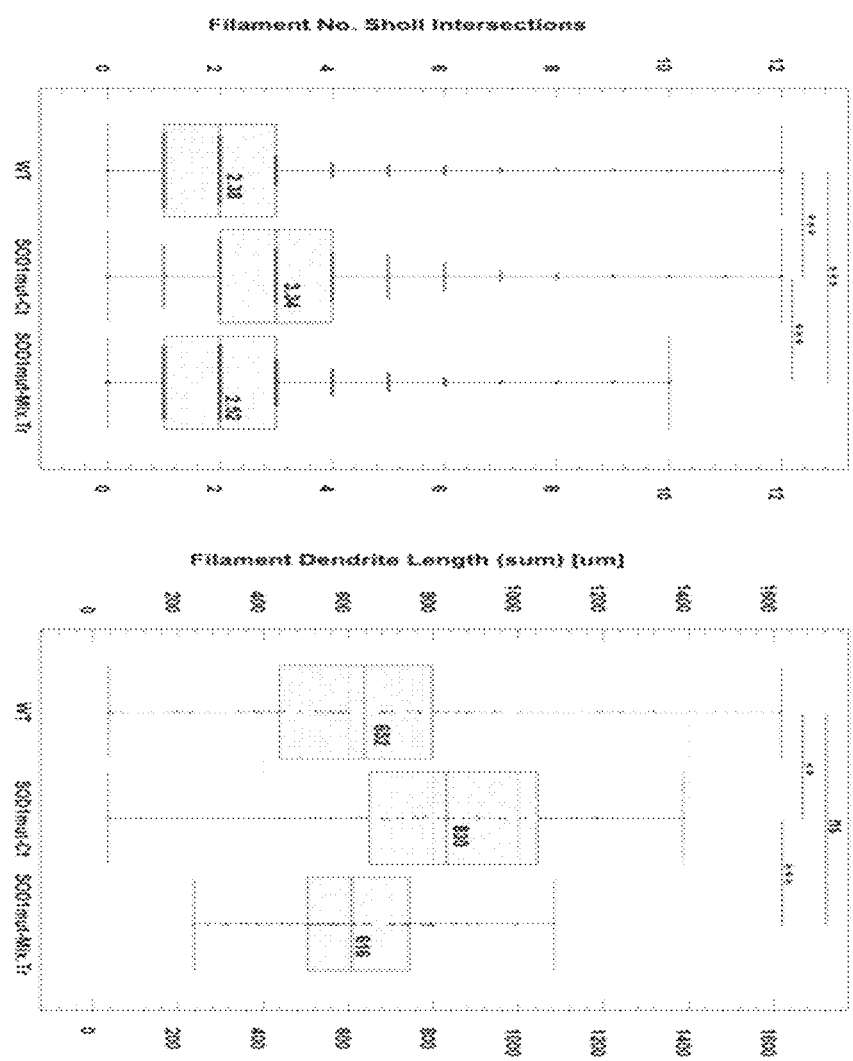

Following these compelling locomotor activity assays results, we conducted morphological assays, analyzing motor neurons morphology following the treatment with the combination of Ciprofloxacin at 100 μM and Celecoxib at 1 μM (FIGS. 14-15). WT zebrafish predominantly exhibited normal motor neurons, with long and moderately branched axons, while the SOD1 mutant showed severe axonopathy with highly complex branched fibers. When treated with the combination of 1 μM Celecoxib and 100 μM Ciprofloxacin, SOD1 mutant larvae showed significant recovery of the mutant morphology, and gained nearly normal axon morphology (FIGS. 14-15). Remarkably, combination of Ciprofloxacin and Celecoxib caused a nearly full recovery of motor neurons axonopathy of SOD1 mutant fish.

This combination of Ciprofloxacin and Celecoxib, as indicated from these pre-clinical studies, may impact neuropathology and degeneration in ALS patients, slowing or inhibiting the disease

EXAMPLE 2 a. Methodology

Fish—Adult and larval zebrafish (*Danio rerio*) were maintained at the Russek-Blum laboratory's fish facility (Dead Sea & Arava Science Center; Yair station, Central Arava) at 28.5° C. and bred according to established procedures[25]. Animal protocols were approved by the Ben Gurion University Committee on Use and Care of Animals. Tg(sod1:sod1G93R or WT; hsp70:DsRed) transgenic lines were used in this study, see Ramesh T, Lyon A N, Pineda R H, et al. *A genetic model of amyotrophic lateral sclerosis in zebrafsh displays phenotypic hallmarks of motoneuron disease. Disease models & mechanisms* 2010; 3:652-62, incorporated herein as a reference. To generate zebrafish expressing transgenic mutant Sod1, a zebrafish genomic region containing the endogenous sod1 promoter and sod1 gene was used. Sod1 was mutated by changing glycine 93 to arginine (G93R); this mutation affects a conserved amino acid that is often mutated in familial ALS, see Orrell R, de Belleroche J, Marklund S, Bowe F, Hallewell R. *A novel SOD mutant and ALS. Nature* 1995; 374:504, and Elshafey A, Lanyon W G, Connor J M. *Identification of a new missense point mutation in exon* 4 *of the Cu/Zn superoxide dismutase (SOD-*1*) gene in a family with amyotrophic lateral sclerosis. Human molecular genetics* 1994; 3:363-4, incorporated herein as references.

Materials and solubility—Celecoxib To achieve high concentration of Celecoxib (Celecoxib BP/EP; batch no. CLX/008/04/17; 25 gr; Prudence Pharma Chem, India), the powder was dissolved to a stock solution of 100 mM in 100% DMSO. The powder was completely dissolved in 100% DMSO, but while diluting the 100 mM Celecoxib stock into final concentration of 100 μM (1:1000) in zebrafish raising buffer (DB), the material precipitated, creating particles and clouds. Celecoxib was then dissolved to a stock solution of 10 mM in 100% DMSO. The powder was completely dissolved in 100% DMSO, and when diluted to final concentration of 30 μM in DB (1:333.3 dilution), the material had stayed in the buffer without crashing. The materials were added to DB in the highest planned concentrations and stored in petri dishes in 28° C. incubator, simulating the exact conditions of the experiment. The final DMSO concentration in the 30 μM Celecoxib in DB was 0.3%. Inspection of the stock solution showed clear solution with no aggregates seen by the naked eye nor under the microscope. In the final diluted solution in DB, no aggregates were observed also after 24 or 48 hrs. Spectrophotometer absorption was observed at 0, 24 and 48 hours after preparation.

Materials and solubility—Ciprofloxacin To achieve high concentration of Ciprofloxacin (Ciprofloxacin hydrochloride Ph,Eur; batch no. CP20517124; 25 gr; Neuland Laboratory LTD, India), the powder was dissolved to a stock solution of 100 mM in ddH2O. The powder was completely dissolved in ddH2O and completely dissolved when diluted to final concentration of 100 μM in DB (1:1000 dilution). The final DMSO concentration in the 100 μM Ciprofloxacin in DB was 0.1%. Inspection of the stock solution showed clear yellow solution with no aggregates seen by the naked eye nor under the microscope. In the final diluted solutions in DB, no aggregates were observed also after 24 or 48 hrs. To adjust the pH to the control sample (0.1% DMSO in DB; pH 6.72), 12 ul of 100 mM NaOH were added to the 100 μM Ciprofloxacin solution (pH 6.32). No addition of NaOH was needed in lower concentration of Ciprofloxacin in DB. Spectrophotometer absorption was analyzed at 0, 24 and 48 hours after preparation (FIG. 3). A light yellow color of the solution caused higher absorption values. Mix of highest concentrations (100 μM Ciprofloxacin+30 μM Celecoxib+NaOH) was measured for absorption in spectrophotometer at 0, 24 and 48 hours after preparation.

Thirty (30) μM Celecoxib had a different absorption compared to the control (DB) of 0.017, 0.013 and 0.021 at 0, 24 and 48 hours after preparation, respectively. 100 μM Ciprofloxacin gave differences in absorption compared to the control of 0.123, 0.149 and 0.155 at 0, 24 and 48 hours after preparation, respectively, due to the clear, light yellow color of the solution. Mix of highest concentrations (100 μM Ciprofloxacin+30 μM Celecoxib) gave differences in absorption compared to the control of 0.16, 0.154 and 0.131 at 0, 24 and 48 hours after preparation, respectively.

Zebrafish raising buffer (DB) used as the basis of all experiments contains final concentrations of: 1.74 mM NaCl, 0.21 mM KCl, 0.12 mM MgSO4, 0.18 mM Ca(NO3)2, 0.15 mM HEPES in ddH2O, final pH=6.7.

Treatment protocol SOD1 G93R mutant or WT fish were collected and raised according to accepted and approved protocols, see Westerfield M. The Zebrafish Book: a Guide for the *Laboratory Use of Zebrafish (Danio rerio)* 2000, incorporated herein as reference. Larvae's morphology was observed (heart rate, overall morphology and behavior) at each day.

FIG. 1 is scheme exhibiting the treatment protocol.

Two-hundred and forty (240) larvae were selected from the same laying batch to be introduced to three distinct treatments and a control (n=60 per each treatment). First and second treatments were conducted at 3 and 5 days post fertilization (dpf), respectively, when the blood brain barrier (BBB) is fully closed, and the motor neurons (MNs) and neuromuscular junctions (NMJs) are fully developed. The materials were administered in the swimming water (DB). At day 6, larvae were taken to behavioral analysis using the automated DanioVision™ system. Following analysis, larvae were fixed and whole-mount immunohistochemistry procedure was conducted to be used for high resolution morphological analysis. Treatment protocol is detailed in FIG. 1.

Toxicity analysis Fish were observed during the day of administration and the following days to observe toxicity. Acute toxicity was evaluated for apoptosis/necrosis and cardiovascular system abnormalities (heart rate, morphology, hemorrhage and edema). Head, eyes and overall morphological and behavioral toxicity were recorded according to accepted procedures[28].

Behavioral analysis DanioVision™, an automated high-throughput tracking system of zebrafish larvae from Noldus Information Technology (Wageningen, the Netherlands), including control of light and dark conditions was used for the measurements and analysis of the results. Each single larvae was put in a single well, with the same volume of swimming water to ensure uniform background. Each animal was tested for its x,y position using dynamic subtraction 30 times per second. The distance each larvae moved in mm was calculated from the x,y position and averaged per time bin of 1 minute (average of 1800 measurements per each 1 minute). The behavioral profile was measured in 3 phases according to changes in environment that we applied, to introduce additional muscle and neurological stress. Spontaneous swimming, light/dark challenge (opto-kinetic response) and recovery from challenge behaviors were recorded and analyzed. All animals from the same treatment: wild type (WT), SOD1 mutant non-treated or treated were averaged per time bin of 1 minute to examine their reaction to additional stress, and then calculated for the whole period of time to get a relative number compared to the non-treated SOD1 mutant swimming behavior. Statistical analysis used was paired Student's t-tests (two-tailed) with two-sample assuming unequal variances. All P-values reported are two-tailed and the significance level was set at 0.05 (*), 0.01 to 0.001 () and below 0.001 (*).

Morphological analysis Whole-mount staining was performed on 6 dpf treated and non-treated SOD1 G93R or WT using anti-acetylated tubulin antibodies using established immunohistochemistry procedures. Spinal motor neuron axonal projections (segments 10-12) stained with anti-acetylated tubulin were imaged using Zeiss apotome microscopy. 3D reconstructed images were used for quantification using the Imaris image analysis software (Bitplane LTD).

b. Results

I. Transgenic SOD1 Mutant Larvae Show Impairments in Locomotor Activity

Larval zebrafish expressing ALS-causing SOD1 G93R mutation were shown previously to have impairments in locomotor activity with abnormal motor axon projections, but otherwise have normal gross morphology, see Lemmens R, Van Hoecke A, Hersmus N, et al. *Overexpression of mutant superoxide dismutase 1 causes a motor axonopathy in the zebrafish*. Human molecular genetics 2007; 16:2359-65, and Ramesh T, Lyon A N, Pineda R H, et al. *A genetic model of amyotrophic lateral sclerosis in zebrafish displays phenotypic hallmarks of motoneuron disease*. Disease models & mechanisms 2010; 3:652-62, incorporated herein as references.

To verify and elaborate our understanding of motor dysfunction in these larvae, we performed video analyses using the DanioVision system, as described in the materials and methods section. Two biological repeats were conducted, analyzing the locomotor activity of 48 animals in each. FIG. 5 depicts the distance moved measured and calculated for 96 SOD1 mutant vs. larvae per time bin of 1 minute.

The parameter analyzed was the distance the larvae moved (in mm). In the first graph all animals-SOD1mut or wild-type (WT) swimming behavior were averaged per time bin of 1 minute to see whether their reaction to additional stress was as expected (FIG. 5).

In all time points averaged, the distance that the WT larvae swam in mm was significantly higher compared to the SOD1 mutant fish. During spontaneous swimming, following light/dark challenge and after recovery from challenge (FIG. 5).

Next, the distances in mm all WT larvae swam in time bin of 1 minute were averaged for the whole period of time to get a relative number compared to the SOD1 mutant swimming behavior (FIG. 6).

During the whole experiment, the distance in mm that the SOD1 mutant larvae swam was significantly reduced compared to the WT larvae. The WT larvae swam nearly 45% more distance than the SOD1 mutants (FIG. 6).

FIG. 6 discloses that SOD1 mutants displayed a significant reduction in their locomotor activity compared to WT during the whole period of measurement.

To analyze the locomotor activity in SOD1 mutants compared to the WT during the different phases of the experiment, following the different responses to stress, we calculated the distance moved per each part of the experiment (FIG. 7). FIG. 7 discloses that SOD mutants displayed a significant reduction in their locomotor activity compared to WT in all 3 phases of the experiment.

When changes in the swimming environment are applied, additional muscle and neurological stress are introduced. During spontaneous swimming (0-10 minutes of the experiment) and light/dark challenge (opto-kinetic response; 10-20 minutes), SOD1 mutants displayed significant reduction in their locomotor activity compared to WT. WT larvae swam 22-28% more than the SOD1 mutants. Following the two peaks of stress (t=10, 20 minutes), a behavior of recovery from challenge was evident. The larvae froze and then gradually recovered back to values of spontaneous swimming. During this phase, SOD1 mutants recovered less efficiently, to a lower locomotor swimming behavior. In this phase, the WT larvae swam 116% more distance than the SOD1 mutants.

II. Verification—Transgenic SOD1 Mutant Larvae Treated with Riluzole Show Elevation in Locomotor Activity Chronic glutamate excitotoxicity may accumulate to toxic levels and contribute to neuronal death in ALS. This provided a rational basis for undertaking a clinical trial with riluzole, a drug with complex effects, but which appears to block the presynaptic release of glutamate. Riluzole demonstrates a modest increase in survival in treated participants (up to 2-3 months) and delays the onset of ventilator-dependence or tracheostomy in selected patients, see Bensimon G, Lacomblez L, Meininger V, Group tARS. *A Controlled Trial of Riluzole in Amyotrophic Lateral Sclerosis*. New England Journal of Medicine 1994; 330:585-91, incorporated herein as a reference.

To determine whether our zebrafish model has the potential to identify novel ALS therapies, we tested the ability of the antiexcitotoxic drug riluzole to modify neuronal stress in the SOD1 mutant zebrafish larvae. Riluzole was chosen for this study as it was for years the only established drug shown to have a disease-modifying effect in ALS patients and since it is the standard of care.

Riluzole was administrated to the swimming water of the SOD1 mutant larvae in a final concentration of 1 μM, a dose that was tested and showed no toxicity in SOD1 mutant zebrafish, see McGown A, Shaw D P J, Ramesh T. *ZNStress: a high-throughput drug screening protocol for identification of compounds modulating neuronal stress in the transgenic mutant sod1G93R zebrafish model of amyotrophic lateral sclerosis*. Molecular neurodegeneration 2016; 11:56, incorporated herein as a reference.

When SOD1 mutants were treated with this concentration of Riluzole, neuronal stress in inhibitory interneurons was reduced, see McGown A, McDearmid J R, Panagiotaki N, et al. *Early interneuron dysfunction in ALS: insights from a mutant sod1 zebrafish model*. Annals of Neurology 2013; 73:246-58, incorporated herein as a reference.

When treated with Riluzole, the distances that the SOD1 mutant larvae swam in mm were higher compared to the non-treated SOD1 mutant fish during all phases of the experiment.

The distances in mm all Riluzole-treated SOD1 mutant larvae swam in a time bin of 1 minute were averaged for the whole period of time to get a relative number compared to the non-treated SOD1 mutant swimming behavior. Riluzole-treated SOD1 mutants displayed a significant elevation in their locomotor activity compared to non-treated SOD1 mutants during the whole period of measurement.

During the whole experiment, the distance in mm that the Riluzole-treated SOD1 mutant larvae swam was significantly higher (elevation of 36.8%) compared to the non-treated SOD1 mutant larvae.

To analyze the locomotor activity in SOD1 mutants compared to the WT during the different phases of the experiments, and following the different responses to stress, we calculated the distance moved per each part of the experiment (FIG. 8).

FIG. 8 discloses that riluzole-treated SOD1 mutants displayed a significant elevation in their locomotor activity compared to non-treated Sod1 mutants in all 3 phases of the experiment.

Treatment with riluzole caused constant elevation in locomotor activity in all phases of the experiment. Riluzole-treated SOD1 mutants displayed significant increase in their locomotor activity compared to non-treated SOD1 mutant larvae during spontaneous swimming (38% increase), light/dark challenge (32% increase) and recovery from challenge (39.7%).

III. Toxicity and Efficacy of Treatment with Celecoxib in ALS (SOD1 Mut) Model

The first material to be tested was the cox2 inhibitor Celecoxib that was suggested to have a role as neuro-inflammatory modulator in maintaining macrophages in their neuroprotective state (see Aïd S, Bosetti F. *Targeting cyclooxygenases-1 and -2 in neuroinflammation: therapeutic implications. Biochimie* 2011; 93:46-51, incorporated herein as reference. Celecoxib was introduced to the swimming water of the SOD1 mutant larvae in three final concentrations, 30 μM, 10 μM and 1 μM. Due to solubility constrains, the experiment was conducted with the background of 0.3% DMSO in all samples (including the control sample).

Summary of section III: While using 0.3% DMSO as a background, Celecoxib caused cardiovascular toxicity and death in the concentration of 30 μM. Subtle locomotor reduction was evident in 10 μM Celecoxib treatment during specific phase of the experiment. Reducing DMSO to 0.1% as a background, caused increase in toxicity produced by Celecoxib. Although the overall morphology and behavior were normal, reduction in locomotor ability was observed below 10 μM Celecoxib and was evident at 5 μM.

Superoxide dismutase enzyme is a central antioxidant catalyst that uses O2− as a substrate (O2− causes a considerable degree of biological damage), reducing its levels into ordinary molecular oxygen (O2) or hydrogen peroxide (H2O2), see Halliwell B, Gutteridge J M C. [1] *Role of free radicals and catalytic metal ions in human disease: An overview. Methods in Enzymology: Academic Press;* 1990: 1-85, incorporated herein as a reference. In vivo, Celecoxib is oxidized by cytochrome P450 (CYP450) 2C9 and 3A4 to the inactive metabolite hydroxycelecoxib, and then hydroxycelecoxib is converted to carboxycelecoxib and celecoxib glucuronide, see Gong L, Thorn C F, Bertagnolli M M, Grosser T, Altman R B, Klein T E. *Celecoxib pathways: pharmacokinetics and pharmacodynamics. Pharmacogenetics and Genomics* 2012; 22:310-8, incorporated herein as a reference. The results showing a shift in toxicity depending on DMSO levels can be explained by a possible hypothesis suggesting a role of DMSO, a powerful scavenger of .OH in protection from Celecoxib toxicity in SOD1 mutants.

Nevertheless, no substantial efficacy was evident using all concentrations of Celecoxib.

IV: Toxicity and Efficacy of Treatment with Ciprofloxacin in ALS (SOD1 Mut) Model The second material to be tested was the Ciprofloxacin previously suggested to enhance DICER activity. Abnormal levels of miRNA are a common molecular mechanism underlying multiple forms of familial and sporadic human ALS and enhancement of DICER activity was found to be beneficial in vivo, see Emde A, Eitan C, Liou L L, et al. *Dysregulated miRNA biogenesis downstream of cellular stress and ALS-causing mutations: a new mechanism for ALS. The EMBO journal* 2015; 34:2633-51, incorporated herein as a reference.

Ciprofloxacin was introduced to the swimming water of the SOD1 mutant larvae in three final concentrations—1 μM, 10 μM and 100 μM. The experiment was conducted on the background of 0.1% DMSO in all samples (including the control sample). In all Ciprofloxacin doses, no drug induced effects in morphology or mortality were observed.

Summary of section IV: The normalized values for each experiment comparing percentage of distance moved of all distinct Ciprofloxacin-treated populations were compared to the non-treated SOD1 mutant larvae. Two main observations can be made. First, ciprofloxacin treatment, even in high doses, was not toxic to SOD1 mutant larvae. Second, it seems that under these study conditions, the 100 μM Ciprofloxacin concentration was the most potent in affecting locomotor activity of the ALS model.

Figure 11:
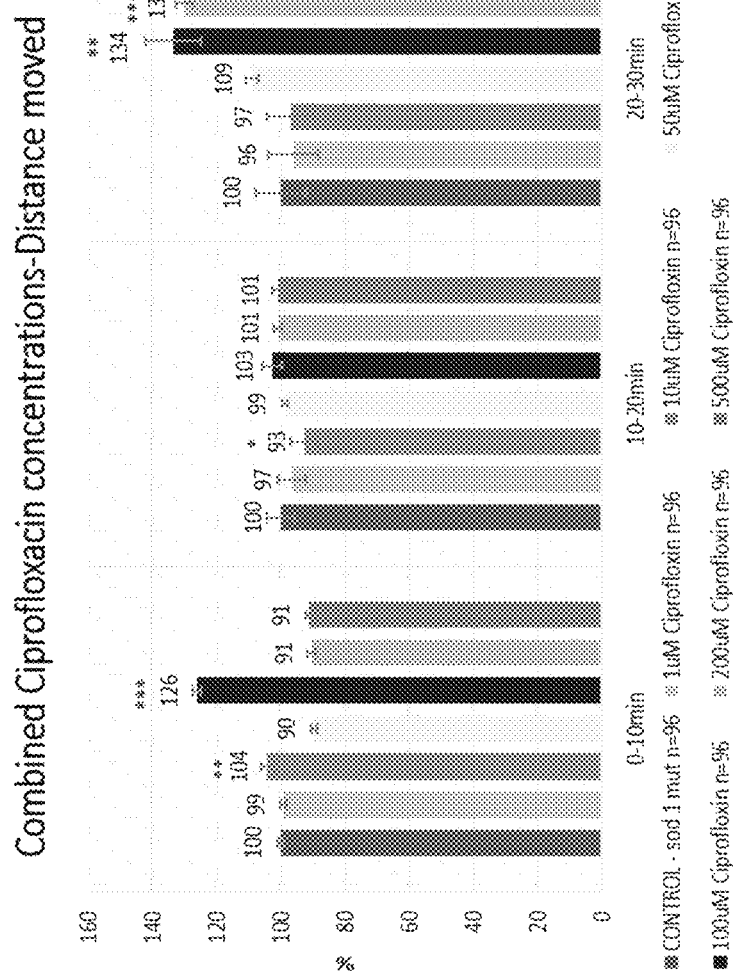
FIG. 11: Summary of locomotor activity of SOD1 mutants treated with Ciprofloxacin distinct concentrations during all 3 phases of the experiment.

Summary of all normalized values representing the percentage of distance moved of Ciprofloxacin-treated vs non-treated SOD1 larvae refining the three phases of the experiment showed unexpected results (FIG. 11).

Treatment with 1, 10, 50, 100, 200 and 500 μM Ciprofloxacin had nearly no effect on locomotor activity of the SOD1 mutant larvae under dark conditions (FIG. 11). In the second phase of light, the phase of recovery from stress, treatment with 50, 100, 200 and 500 μM Ciprofloxacin gave a dose dependent curve that eventually ended in a plateau. ANOVA and t-test static studies showed no statistically significant change between the 200 and 500 μM Ciprofloxacin treatments (the statistics presented is significance from non-treated).

During the period of spontaneous swimming, only a dose of 100 μM Ciprofloxacin caused elevated swimming behavior (FIG. 11). Two possible explanations can underlie the fact that 200 and 500 μM Ciprofloxacin treatment did not cause elevation in spontaneous swimming of SOD1 mutants: subtle burden on swimming ability due to high Ciprofloxacin concentrations or, although less reasonable, elevated levels of NaCl salt in the swimming media (or both). To adjust pH levels to that of the control group (no Ciprofloxacin), NaOH was added to a final concentration of 0.06 mM in the 50 and 100 μM Ciprofloxacin treatments, 0.135 mM and 0.32 mM NaOH in the 200 μM and 500 μM Ciprofloxacin treatments, respectively.

FIG. 11 discloses a summary of locomotor activity of SOD1 mutants treated with Ciprofloxacin distinct concentrations during all 3 phases of the experiment V. Toxicity and Efficacy of Treatment with Celecoxib and Ciprofloxacin Combinations in ALS (SOD1 Mut) Model Combining cox2 inhibitor Celecoxib that was suggested to have a role as neuro-inflammatory modulator in maintaining macrophages in their neuroprotective state[23] with Ciprofloxacin which has been previously suggested to enhance DICER activity to attenuate miRNA abnormal levels, see Emde A, Eitan C, Liou L L, et al. *Dysregulated miRNA biogenesis downstream of cellular stress and ALS-causing mutations: a new mechanism for ALS. The EMBO* journal 2015; 34:2633-51, incorporated herein as a reference, was of interest, as they both tackle two main mechanisms underlying ALS. Furthermore, synergistic activity of both agents has been demonstrated, see Dey R, Sultana S, Bishayi B. *Combination treatment of celecoxib and ciprofloxacin attenuates live S. aureus induced oxidative damage and inflammation in murine microglia via regulation of cytokine balance. J Neuroimmunol* 2018; 316:23-39, incorporated herein as a reference.

Due to toxic limitation in the use of Celecoxib, we decided to use 1, 4 and 10 µM Celecoxib in combination with the most potent concentration of Ciprofloxacin (100 µM). The experiment was conducted on the background of 0.1% DMSO in all samples.

In all combinations used (100 µM Cipro+1 µM Celecoxib; 100 µM Cipro+4 µM Celecoxib; 100 µM Cipro+10 µM Celecoxib), no cardiovascular system abnormalities (heart rate, morphology, hemorrhage and edema) or mortality were observed. Treating SOD1 mutant larvae with the highest concentration of Celecoxib with Ciprofloxacin (100 µM Cipro+10 µM Celecoxib) had visible effect on their swimming ability under the microscope. The larvae swam shorter distances and fell on their side between movements. No obvious abnormalities in movement were evident in SOD1 mutant larvae treated with the combinations containing lower Celecoxib doses (100 µM Cipro+1 µM Celecoxib; 100 µM Cipro+4 µM Celecoxib).

The averaged distance that treated larvae moved per time bin of 1 minute was analyzed using the EthoVision software.

The abnormal movement observed under the microscope in the 100+10 mix (100 µM Cipro+10 µM Celecoxib)-treated SOD1 mutant larvae was evident; the larvae swam shorter distances during the spontaneous swimming and light/dark challenge periods. The mix containing the lowest Celecoxib concentration 100+1 mix (100 µM Cipro+1 µM Celecoxib) gave substantial improvement in SOD1 mutant swimming ability during all behavioral response profiles.

Next, the distance in mm all larvae from the same treatment swam in time bin of 1 minute was averaged for the whole period of time to get a relative number compared to the non-treated SOD1 mutant swimming behavior (FIG. 4). FIG. 4 depicts ciprofloxacin and celecoxib combinations—treated SOD1 mutants' locomotor activity compared to non-treated SOD1 mutants during the whole period of measurement.

As a whole, the SOD1 mutants treated with the 100+1 mix showed dramatic and significant improvement in swimming ability (28.8%, FIG. 4). SOD1 mutants treated with the 100+4 mix showed significant improvement in their swimming ability, albeit lower than the 10+1 mix (14.9%). SOD1 mutants treated with 100+10 mix showed significant reduction in their swimming behavior (decrease of 20.7%, FIG. 4).

The distance moved per each part of the experiment was calculated and compared to the non-treated SOD1 mutant swimming behavior (FIG. 3). FIG. 3 depicts Ciprofloxacin and Celecoxib combinations—treated SOD1 mutants' locomotor activity compared to non-treated SOD1 mutants in all 3 phases of the experiment. In all three phases of the experiment, efficacy of the distinct combinations was dose dependent, with higher potency as Celecoxib doses decreased in the mix (FIG. 3). SOD1 mutants treated with the 100+1 mix showed outstanding improvement in their swimming ability during spontaneous swimming (25.3%), light/dark challenge (11.8%) and most dramatically during recovery from challenge (72.2% !).

SOD1 mutants treated with the 100+4 mix showed less but yet significant increase in their swimming ability during spontaneous swimming (14.5%) and recovery from challenge (42.8%). Treatment with 100+10 mix caused statistically significant reduction in locomotor activity of the SOD1 mutant larvae during spontaneous swimming (31.4% decrease) and light/dark challenge (29.4% decrease). During recovery from challenge, increase of 17.7% was evident even in the 100+10 mix (FIG. 3).

As the combination of 100 µM Cipro and 1 µM Celecoxib gave such substantial improvement in SOD1 mutant swimming ability, it was decided to further check its effect on SOD1 mutant larvae using morphological assays.

VI: Morphological Analysis of Ventral Motor Neuron Following Treatment with Celecoxib and Ciprofloxacin Combination in ALS (SOD1 Mut) Model ALS zebrafish models mutated in distinct ALS-associated genes such as TDP-43, FUS, C9orf72, Sqstm1, EPHA4 and SOD1, exhibit motor axons phenotype consisting of disorganized, excessively branched motor neuronal axons as well as swimming deficits, see Kabashi E, Bercier V, Lissouba A, et al. *FUS and TARDBP but Not SOD1 Interact in Genetic Models of Amyotrophic Lateral Sclerosis. PLoS genetics* 2011; 7:e1002214; Lemmens R, Van Hoecke A, Hersmus N, et al. *Overexpression of mutant superoxide dismutase 1 causes a motor axonopathy in the zebrafsh. Human molecular genetics* 2007; 16:2359-65; Lattante S, de Calbiac H, Le Ber I, Brice A, Ciura S, Kabashi E. *Sqstm1 knock-down causes a locomotor phenotype ameliorated by rapamycin in a zebrafish model of ALS/FTLD. Human molecular genetics* 2015; 24:1682-90; Sorana C, Serena L, Isabelle L B, et al. *Loss of function of C9orf72 causes motor deficits in a zebrafish model of amyotrophic lateral sclerosis. Annals of neurology* 2013; 74:180-7, Van Hoecke A, Schoonaert L, Lemmens R, et al. *EPHA4 is a disease modifier of amyotrophic lateral sclerosis in animal models and in humans. Nature medicine* 2012; 18:1418; Sakowski S A, Lunn J S, Busta A S, et al. *Neuromuscular effects of G93A-SOD1 expression in zebrafish. Molecular neurodegeneration* 2012; 7.44; Armstrong G A B, Liao M, You Z, Lissouba A, Chen B E, Drapeau P. *Homology Directed Knockin of Point Mutations in the Zebrafish tardbp and fus Genes in ALS Using the CRISPR/Cas9 System. PLoS one* 2016; 11:e0150188, incorporated herein as references.

We used immunostaining, apotome microscopy and Imaris image analysis software to characterize motor neurons morphology in WT, non-treated SOD1 G93R mutants and SOD1 G93R mutants treated with the 100 µM Cipro+1 µM Celecoxib combination (FIG. 14).

WT zebrafish predominantly exhibited normal motor neurons, with long and moderately branched axons (FIG. 14, left panel).

The SOD1 G93R mutant larvae, all originating from the same laying batch, were divided into two groups, treated (half with DMSO only and half with the mix), stained and imaged. The ALS model SOD1 mutant control group (untreated, 0.1% DMSO) showed severe axonopathy with highly complex branched fibers (FIG. 14, middle panel). Remarkably, the half of SOD1 mutant larvae that were treated with the combination of 1 µM Celecoxib and 100 µM Ciprofloxacin showed significant recovery of the mutant morphology, and gained nearly normal axon morphology (FIG. 14, left panel).

In summary, FIG. 14 discloses that administration of Ciprofloxacin and Celecoxib recovered axonopathy of SOD1 mutant fish. Morphological analysis of individual motor neurons in the trunk of zebrafish larva; segments S10-S12 were used for analysis. Left panel—WT, middle panel—non-treated SOD1 mutant fish, left panel—1 µM Celecoxib+100 µM Ciprofloxacin-treated SOD1 mutant fish. Upper panel—3D reconstructed apotome z-stack images of branching motor neurons in the trunk of 6 dpf zebrafish larvae immunostained with anti-acetylated tubulin antibodies. Middle and lower panels—The backbone (colored processes) of motor neurons traced with the Filaments analysis of Imaris software (Bitplane; in white—single motor neuron backbone). n=15; control and treated SOD1 mutants and n=11; WT fish.

High-resolution image analyses were conducted using the Imaris software to compare distinct parameters of axons morphology (FIG. 15). All examined parameters showed reduction in axonopathy in the 1 µM Celecoxib and 100 µM Ciprofloxacin-treated SOD1 mutant fish compared to non-treated SOD1 mutants, including area, branching level, branch points (junctions), segments, length and their spreading in Sholl analysis and showed significant recovery towards the wild type axon morphology (FIG. 15).

Combination of Ciprofloxacin and Celecoxib caused a nearly full recovery of motor neurons axonopathy of SOD1 mutant fish. In summary, FIG. 15 depicts that combination of ciprofloxacin and celecoxib caused a nearly full recovery of motor neurons axonopathy of SOD1 mutant fish. Aspects of length and branching of motor neurons axonal projections were calculated using the Imaris software (Bitplane) and are plotted in the graphs.

VII. Comparing Efficacy of Treatment with Enoxacin vs Ciprofloxacin in ALS (SOD1 Mut) Model Enoxacin is a small molecule from the quinolone family that enhances siRNA-mediated mRNA degradation and promotes the biogenesis of endogenous miRNAs, see Melo S, Villanueva A, Moutinho C, et al. *Small molecule enoxacin is a cancer-specific growth inhibitor that acts by enhancing TAR RNA-binding protein 2-mediated microRNA processing*. Proceedings of the National Academy of Sciences of the United States of America 2011; 108:4394-9, and Shan G, Li Y, Zhang J, et al. *A small molecule enhances RNA interference and promotes microRNA processing. Nature biotechnology* 2008; 26:933-40, incorporated herein as references. Both in vitro and in vivo ALS models showed benefit when treated with Enoxacin, see Emde A, Eitan C, Liou L L, et al. *Dysregulated miRNA biogenesis downstream of cellular stress and ALS-causing mutations: a new mechanism for ALS. The EMBO journal* 2015; 34:2633-51, and Shan G, Li Y, Zhang J, et al. *A small molecule enhances RNA interference and promotes microRNA processing. Nature biotechnology* 2008; 26:933-40, incorporated herein as references. Ciprofloxacin, another quinolone family member, is commercially available and was shown to have substantial RNAi-enhancing activity. Its effect was slightly lesser than Enoxacin in in vitro RNAi reporter assays, see Shan G, Li Y, Zhang J, et al. *A small molecule enhances RNA interference and promotes microRNA processing. Nature biotechnology* 2008; 26:933-40, incorporated herein as a reference. In this study, Ciprofloxacin showed a significant improvement in the swimming activity of SOD1 mutant larvae (FIG. 10).

To examine the hypothesis that Ciprofloxacin, like Enoxacin, may contribute to ALS model in vivo, we set out to compare Enoxacin and Ciprofloxacin effect on motor ability of the SOD1 G93R zebrafish mutant.

Enoxacin was introduced to the swimming water of the SOD1 mutant larvae in two final concentrations—10 µM and 100 µM. The experiment was conducted on the background of 0.1% DMSO in all samples.

In both Enoxacin doses, no drug induced effects in morphology or mortality were observed. The averaged distance that treated larvae moved per time bin of 1 minute was analyzed. Treatment with 100 µM Enoxacin caused increase in locomotor activity of ALS larvae. Dose of 10 µM Ciprofloxacin did not significantly affect locomotor activity of the treated mutant larvae throughout the experiment. A very similar dose effect was seen in Ciprofloxacin-treated larvae.

During the whole experiment, the distance in mm that the 10 µM enoxacin-treated SOD1 mutant larvae swam was not changed compared to the non-treated SOD1 mutant larvae. The SOD1 mutants treated with 100 µM enoxacin showed substantial increase in their swimming behavior (19.9%). Similarly, during the whole experiment, the distance in mm that the 10 µM Ciprofloxacin-treated SOD1 mutant larvae swam was not changed compared to the non-treated SOD1 mutant larvae, while the SOD1 mutants treated with 100 µM Ciprofloxacin showed substantial increase in their swimming behavior (17.8%).

Figure 12:
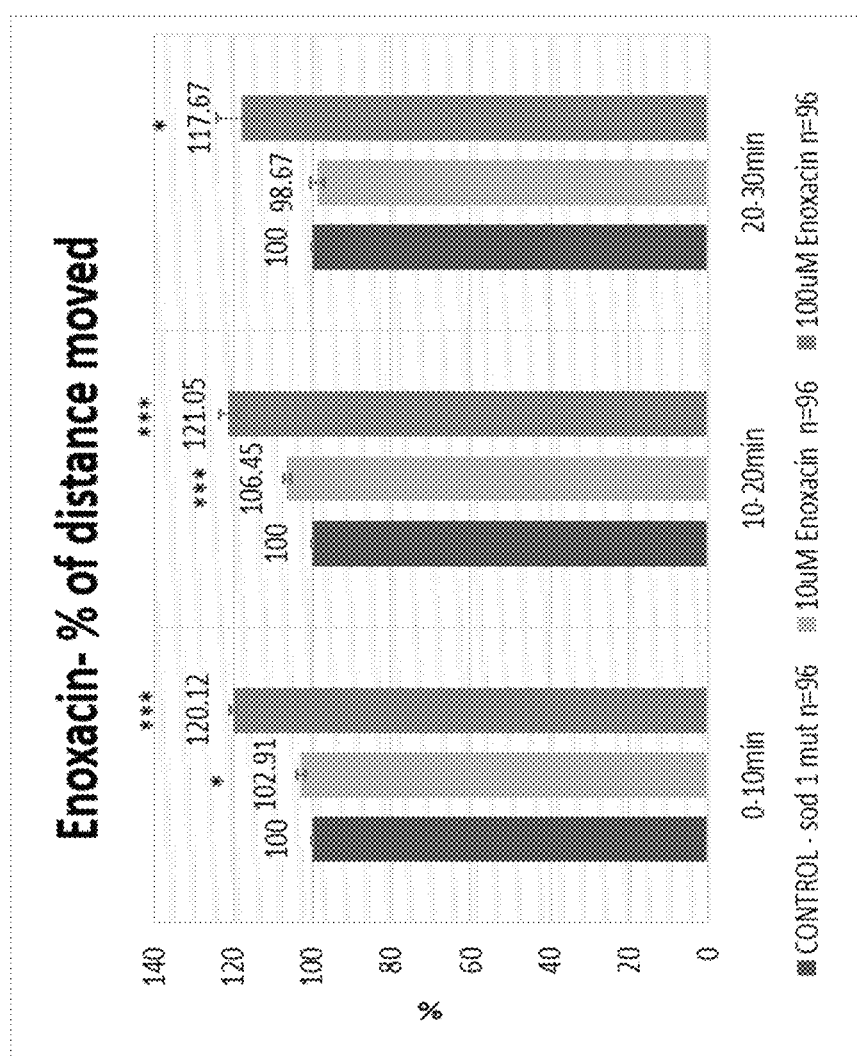
FIG. 12: Enoxacin-treated SOD1 mutants' locomotor activity compared to non-treated SOD1 mutants in all 3 phases of the experiment.

The distance moved per each part of the experiment was calculated and compared to the non-treated SOD1 mutant swimming behavior (FIG. 12). Treatment with 10 µM enoxacin had nearly no effect on locomotor activity of the SOD1 mutant larvae during spontaneous swimming, light/dark challenge and recovery from second challenge. Treatment with 100 µM enoxacin showed significant increase in locomotor activity in the phase of spontaneous swimming (20.1%), light/dark challenge (21%) and following recovery from challenge (17.6%, FIG. 12).

FIG. 12 depicts enoxacin-treated SOD1 mutants' locomotor activity compared to non-treated SOD1 mutants in all 3 phases of the experiment.

Correspondingly, treatment with 10 µM Ciprofloxacin had nearly no effect on locomotor activity of the SOD1 mutant larvae during all three experimental phases (FIG. 10). Treatment with 100 µM Ciprofloxacin showed significant increase in locomotor activity in the phase of spontaneous swimming (26.2%) and following recovery from challenge (33.5%).

Figure 13:
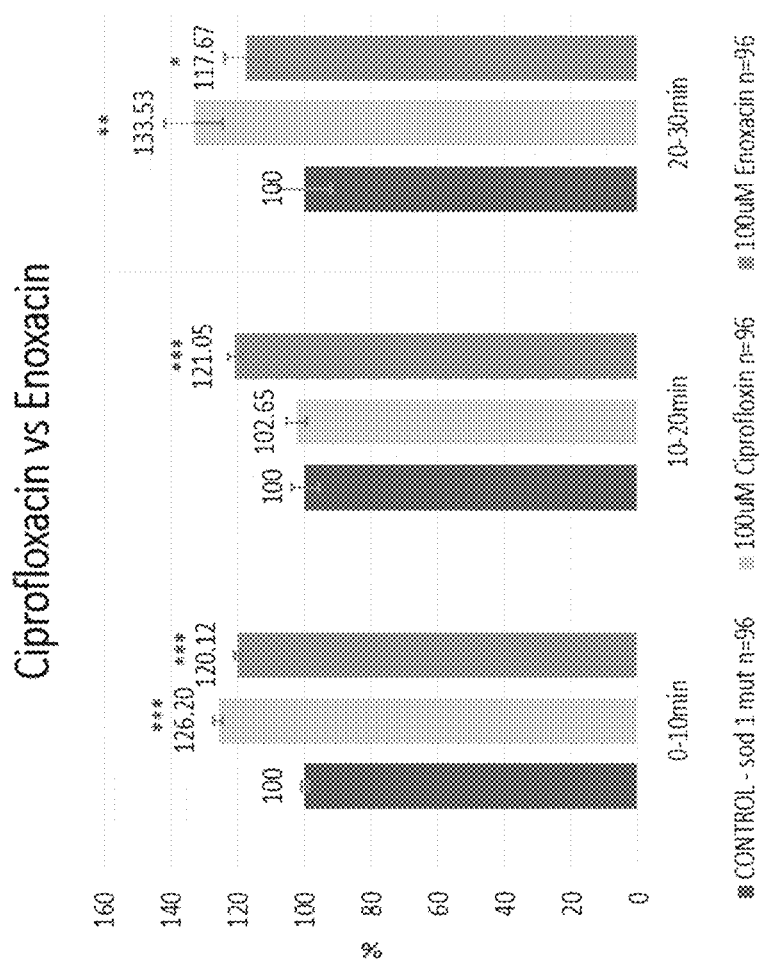
FIG. 13: Normalized enoxacin vs Ciprofloxacin-treated SOD1 mutants' locomotor activity compared to non-treated SOD1 mutants in all 3 phases of the experiment.

To conclude this part, comparisons between treatments with 100 µM ciprofloxacin and 100 µM enoxacin are presented in FIG. 13. FIG. 13 depicts normalized enoxacin vs Ciprofloxacin-treated SOD1 mutants' locomotor activity compared to non-treated SOD1 mutants in all 3 phases of the experiment.

First, both enoxacin and Ciprofloxacin caused similar overall increase in locomotor activity of SOD1 mutant larvae in the same range of concentrations. Second, treating SOD1 mutants with Ciprofloxacin caused elevated locomotor activity compared to Enoxacin treatment during both spontaneous swimming and recovery from challenge (FIG. 13).

EXAMPLE 3

Autism A common strategy in establishing connection specificity of the nervous system is for neurons to develop exuberant axonal and dendritic processes, followed by selective pruning of a subset of processes. For example, long-distance projection neurons from layer V of the mammalian cortex send axon branches to both the spinal cord and the superior colliculus during an early stage of development. Later in development, motor cortical neurons selectively prune their branches to the superior colliculus, whereas visual cortical neurons selectively prune their branches to the spinal cord. Axon pruning is widely used for the refinement of neural circuits in both vertebrates and invertebrates, and may also contribute to the pathogenesis of neurodegenerative diseases, see Watts, R. J., Hoopfer, E. D., & Luo, L. (2003). *Axon pruning during Drosophila metamorphosis: evidence for local degeneration and requirement of the*

*ubiquitin-proteasome system. Neuron,* 38(6), 871-885, incorporated herein as reference.

Autism spectrum disorders (ASDs) are neurodevelopmental disorders characterized by impaired social interaction, communication deficits, repetitive behaviors, and narrow and intense interests. Increased dendritic spine density has been found in ASD brains and abnormal synaptic structures were observed in ASD model mice.

As described in the previous paragraph, postnatal synaptic development is dynamically regulated by concurrent synapse formation and elimination in the mammalian cerebral cortex. The extra and unnecessary synapses formed early in development are subsequently eliminated and a subset of synapses is maintained and strengthened. Hence, precise regulation of synapse formation and elimination is important for the normal development of the brain, while reduced elimination of synapses, resulting in an excess, is thought to be associated with neurodevelopmental disorders such as ASD, see Kim, H-J et al. *"Deficient Autophagy in Microglia Impairs Synaptic Pruning and Causes Social Behavioral Defects." Molecular Psychiatry* 22.11 (2017): 1576-1584, incorporated herein as reference.

The present invention discloses a severe axonopathy mainly characterized highly complex branched motor neurons in SOD1 G93R zebra fish mutant. The composition of the present invention, specifically the combination of ciprofloxacin and celecoxib, showed recovery of this motor neurons axonopathy, and significant reduction in overall branching as well as branching, level, branching points and branching area. These findings resemble reduction of branching essential for postnatal synaptic development and suggest a possible treatment modality for autism (see FIG. 15A, 15B, 15C).

EXAMPLE 4

The combination of the fluoroquinolone and the anti-inflammatory is formulated to either oral administration, intravenous administration or topical administration.

The formulations of the present invention comprise inter alia, in a non-limiting matter, additional ingredients or pharmaceutical excipients to further develop a formula to have a desired concentration, effective doses, dosing regiments and treatment times. These ingredients include, inter alia, solubilizers, stabilizers, buffers, tonicity modifiers, bulking agents, viscosity enhancers/reducers, surfactants, chelating agents, and adjuvants.

Oral administration Oral drugs are taken as tablets or capsules.

Tablets: The dissolution of the tablet can be affected significantly by particle size and crystal form. The dissolution time can be modified for a rapid effect (fast dissolution) or for sustained release, (slow dissolution rates which prolong the duration of action or avoid initial high plasma levels).

Capsules: A capsule is a gelatinous envelope enclosing the active substance. Capsules can be designed to remain intact for some hours after ingestion in order to delay absorption. They may also contain a mixture of slow- and fast-release particles to produce rapid and sustained absorption in the same dose.

Oral sustained release: Oral sustained release in capsules or tablets is achieved, in a non-limiting matter, by embedding the active ingredient in an insoluble porous matrix, such that the dissolving drug must make its way out of the matrix before it can be absorbed. sustained release formulations in which the matrix swells to form a gel through which the drug exits, or by an osmotic controlled-release oral delivery system, where the active compound is encased in a water-permeable membrane with a laser drilled hole at one end. As water passes through the membrane the drug is pushed out through the hole and into the digestive tract where it can be absorbed.

Solutions: Pharmaceutical solutions are extensively used as dosage forms for the oral administration of therapeutic agents. Pharmaceutical solutions defined as liquid preparations in which the therapeutic agent and the various excipients are dissolved in the chosen solvent system. Pharmaceutical solutions are homogeneous, i.e. the therapeutic agent(s) and excipients are dissolved in the vehicle Parenteral administration: Parenteral administration is performed using intravenous, subcutaneous, intramuscular, and intra-articular administration. The drug is stored in liquid or if unstable, lyophilized form.

Topical administration: Topical formulations comprise inter alia cream, ointment, paste, lotion or gel.

Transdermal delivery: Transdermal delivery is achieved, for example, by transdermal patches.

Alternative routes of administration are suppository, intraventricular, intramuscular, inhalational, aerosol, and sublingual.

EXAMPLE 5

The composition of the current invention is used in the aforementioned ratios of combinations of: Weight/weight daily human doses.

TABLE 1

Weight/weight combination for Ciprofloxacin and Celecoxib

| Combination # | Ciprofloxacin | Celecoxib |
| --- | --- | --- |
| 1 | 1 mg-50 mg | 1 mg-50 mg |
| 2 | 1 mg-50 mg | 50 mg-100 mg |
| 3 | 1 mg-50 mg | 100 mg-200 mg |
| 4 | 1 mg-50 mg | 200 mg-600 mg |
| 5 | 1 mg-50 mg | 600 mg-1200 mg |
| 6 | 50 mg-100 mg | 1 mg-50 mg |
| 7 | 50 mg-100 mg | 50 mg-100 mg |
| 8 | 50 mg-100 mg | 100 mg-200 mg |
| 9 | 50 mg-100 mg | 200 mg-600 mg |
| 10 | 50 mg-100 mg | 600 mg-1200 mg |
| 11 | 100 mg-200 mg | 1 mg-50 mg |
| 12 | 100 mg-200 mg | 50 mg-100 mg |
| 13 | 100 mg-200 mg | 100 mg-200 mg |
| 14 | 100 mg-200 mg | 200 mg-600 mg |
| 15 | 100 mg-200 mg | 600 mg-1200 mg |
| 16 | 200 mg-600 mg | 1 mg-50 mg |
| 17 | 200 mg-600 mg | 50 mg-100 mg |
| 18 | 200 mg-600 mg | 100 mg-200 mg |
| 19 | 200 mg-600 mg | 200 mg-600 mg |
| 20 | 200 mg-600 mg | 600 mg-1200 mg |
| 21 | 600 mg-1200 mg | 1 mg-50 mg |
| 22 | 600 mg-1200 mg | 50 mg-100 mg |
| 23 | 600 mg-1200 mg | 100 mg-200 mg |
| 24 | 600 mg-1200 mg | 200 mg-600 mg |
| 25 | 600 mg-1200 mg | 600 mg-1200 mg |
| 26 | 1200 mg-2000 mg | 1 mg-50 mg |
| 27 | 1200 mg-2000 mg | 50 mg-100 mg |
| 28 | 1200 mg-2000 mg | 100 mg-200 mg |
| 29 | 1200 mg-2000 mg | 200 mg-600 mg |
| 30 | 1200 mg-2000 mg | 600 mg-1200 mg |

EXAMPLE 6

A synopsis of a clinical trial for evaluation the therapeutic effect of a combination of celecoxib and ciprofloxacin.

As used herein after, the term "Prime C" generally refers hereinafter to a composition comprising a combination of celecoxib and ciprofloxacin.

TABLE 2

| | synopsis for a clinical trial |
|---|---|
| Title | A Phase 2, Multi-Center, Double-Blind, Randomized, Placebo-Controlled Study to Evaluate the Safety, Tolerability, and Efficacy of Prime_C in Patients with Amyotrophic Lateral Sclerosis (ALS) |
| Indication | Amyotrophic Lateral Sclerosis (ALS) |
| Study Population | Patients with a diagnosis of ALS for less than 24 months |
| Primary Objective | To assess the effect of Prime_C versus placebo on respiratory function in patients with ALS |
| Primary Endpoint | The change from baseline to Visit Week 24 in EIM 150 Hz phase of the fastest changing muscle in active treatment vs placebo at 24 weeks |
| Secondary Objectives | 1. To assess the effect of Prime_C versus placebo on the HHD0 time to failure endpoint using HHD<br>2. To assess the effect of Prime_C versus placebo on vital capacity as assessed at home twice weekly<br>3. To assess the effect of Prime_C versus placebo on ALSFRS-R as assessed at home twice weekly<br>4. To assess the effect of Prime_C versus placebo on vital capacity and ALSFRS-R at baseline compared to week 24<br>5. To assess safety and tolerability of Prime_C 1 in patients with ALS<br>6. To assess changes in pNFH in csf and in blood from baseline to week 24 in patients on Prime_C vs placebo<br>7. To assess changes in miRNAs in csf and in blood from baseline to week 24 in patients on Prime_C vs placebo |
| Secondary Endpoints | 1. Time to first zero muscle strength (HHD0) in Prime_C 1 patients compared to placebo<br>2. Change in slope from baseline to Visit Week 24 in vital capacity measured at home twice weekly in patients on Prime_C 1 compared to placebo<br>3. Change in slope from baseline to Visit Week 24 in ALSFRS-R measured at home twice weekly in patients on Prime_C 1 compared to placebo<br>4. Change in slope from baseline to Visit Week 24 in the ALS Functional Rating Scale - Revised (ALSFRS-R) and vital capacity measured at study visits in patients on Prime_C compared to placebo<br>5. Subject incidence of adverse events in patients on Prime_C compared to placebo<br>6. Change in pNFH in csf and in blood from baseline to week 24 in patients on Prime_C 1 vs placebo<br>7. Change in miRNAs in csf and in blood from baseline to week 24 in patients on Prime_C 1 vs placebo |
| Safety Measurements | 1. Adverse events<br>2. Vital signs<br>3. Clinical laboratory parameters<br>4. ECG parameters<br>5. Physical and neurological examinations<br>6. Suicidality assessment |
| Study Overview | This is a Phase 2, double-blind, randomized, placebo-controlled, multiple dose study of Prime_C in patients with ALS.<br>Randomization will be 1:1, Prime_C vs placebo. Within each cohort, randomization will be stratified by riluzole and edaravone use. The screening and qualification period for the study will be no more than 14 days in duration. Once patients have completed screening and are considered eligible for the study, they will be randomized as described above, stratified by riluzole use.<br>There will be a total of 7 study visits for patients in each cohort:<br>Screening<br>Start of Dosing (Day 1)<br>Week 8 (Day 57)<br>Week 16 (Day 113)<br>Week 24 (Day 169)<br>Telephone follow-up Visit (4 weeks after last dose of study drug) |
| Number of Patients | Approximately 200 patients with ALS will be screened in order to enroll at least 150 patients with ALS. |
| Estimated Study Duration | Individual patient participation will last approximately 26 weeks, divided as follows:<br>1. Screening and qualification period: up to 2 weeks<br>2. Double-blind treatment, safety, and efficacy assessment period for 24 weeks of dosing<br>Total study duration is anticipated to be up to 24 months, with 18 months allocated for study start-up and patient recruitment. |

TABLE 2-continued synopsis for a clinical trial

| | |
|---|---|
| Study Assessments | EIM<br>HHD muscle testing<br>VC<br>AL SFRS-R<br>SVC |

EIM—Electric Impedance Myography,
HHD—Hand-Held Dynamometers,
VC—Vital Capacity,
ALSFRS-r—ALS Functional Rating Scale revised, and
SVC—Slow Vital Capacity.

Although described above in connection with particular embodiments of the present invention, it should be understood that the descriptions of the embodiments are illustrative of the invention and are not intended to be limiting. Various modifications and applications may occur to those skilled in the art without departing from the true spirit and scope of the invention.

The invention claimed is:

1. A method for treating a subject having amyotrophic lateral sclerosis, comprising:
   administering to the subject a formulation comprising a therapeutically effective amount of synergistic combination of celecoxib and ciprofloxacin, and
   wherein the therapeutically effective amount slows or inhibits progression of amyotrophic lateral sclerosis in the subject.

2. The method of claim 1, wherein the celecoxib to the ciprofloxacin ratio is about 1:10.

3. The method of claim 1, wherein the formulation is administered orally to the subject having amyotrophic lateral sclerosis.

4. The method of claim 1, wherein the formulation is administered once daily.

5. The method of claim 1, wherein the formulation is administered twice daily.

6. The method of claim 1, wherein the formulation is sustained release formulation.

7. The method of claim 1, wherein the formulation is a tablet.

8. The method of claim 1, wherein the formulation comprises 100-200 mg celecoxib and 1200-2000 mg ciprofloxacin.

9. The method of claim 1, wherein the formulation is an oral sustained release formulation and wherein the celecoxib and the ciprofloxacin are embedded into a porous matrix.

10. The method of claim 1, wherein the celecoxib and the ciprofloxacin are administered sequentially or concomitantly.

11. The method of claim 1, wherein the celecoxib to the ciprofloxacin ratio ranges from about 10:1 to about 1:1000.

12. The method of claim 1, wherein the celecoxib to the ciprofloxacin ratio ranges from about 1:1 to about 1:200.

13. The method of claim 1, wherein the celecoxib to the ciprofloxacin ratio ranges from about 1:10 to about 1:200.

14. The method of claim 1, wherein the celecoxib to the ciprofloxacin ratio is about 1:1 to about 1:10.

15. The method of claim 1, wherein the subject is a human.

16. The method of claim 15, wherein a celecoxib dose ranges from about 10 mg to about 800 mg daily and a ciprofloxacin dose ranges from about 50 mg to about 2000 mg daily.

17. The method of claim 15, wherein the celecoxib daily dose ranges from 1 mg to 50 mg.

18. The method of claim 15, wherein the celecoxib daily dose ranges from 50 mg to 100 mg.

19. The method of claim 1, wherein the ciprofloxacin is ciprofloxacin-HCl.

* * * * *